US011079386B2

(12) United States Patent
Harada et al.

(10) Patent No.: US 11,079,386 B2
(45) Date of Patent: Aug. 3, 2021

(54) MONOCLONAL ANTIBODY AGAINST FZD10 AND USE THEREOF

(71) Applicant: ONCOTHERAPY SCIENCE, INC., Kawasaki (JP)

(72) Inventors: Yosuke Harada, Kawasaki (JP); Tatsuki Yokoseki, Kawasaki (JP); Yusuke Nakamura, Kawasaki (JP)

(73) Assignee: ONCOTHERAPY SCIENCE, INC., Kawasaki (JP)

( * ) Notice: Subject to any disclaimer, the term of this patent is extended or adjusted under 35 U.S.C. 154(b) by 112 days.

(21) Appl. No.: 16/336,846

(22) PCT Filed: Oct. 4, 2017

(86) PCT No.: PCT/JP2017/036081
§ 371 (c)(1),
(2) Date: Mar. 26, 2019

(87) PCT Pub. No.: WO2018/066585
PCT Pub. Date: Apr. 12, 2018

(65) Prior Publication Data
US 2020/0174002 A1 Jun. 4, 2020

(30) Foreign Application Priority Data
Oct. 6, 2016 (JP) .............................. JP2016-197881

(51) Int. Cl.
*G01N 33/574* (2006.01)
*C07K 16/28* (2006.01)

(52) U.S. Cl.
CPC ... *G01N 33/57492* (2013.01); *C07K 16/2863* (2013.01); *C07K 2317/565* (2013.01)

(58) Field of Classification Search
CPC ........... G01N 33/57492; G01N 33/574; G01N 2800/52; C07K 16/2863; C07K 2317/565; C07K 16/28
See application file for complete search history.

(56) References Cited

U.S. PATENT DOCUMENTS

| | | |
|---|---|---|
| 2003/0044409 A1 | 3/2003 | Carson et al. |
| 2003/0215449 A1 | 11/2003 | Mezes et al. |
| 2004/0247593 A1 | 12/2004 | He et al. |
| 2005/0272063 A1* | 12/2005 | Nakamura ............... A61P 35/00 435/5 |
| 2006/0024692 A1 | 2/2006 | Nakamura et al. |
| 2009/0175844 A1 | 7/2009 | Nakamura et al. |
| 2012/0014996 A1 | 1/2012 | Nakamura et al. |
| 2013/0011933 A1 | 1/2013 | Nakamura et al. |

FOREIGN PATENT DOCUMENTS

| | | |
|---|---|---|
| EP | 1648506 B1 | 2/2012 |
| JP | 2007-526891 A | 9/2007 |
| JP | 2009-541204 A | 11/2009 |
| RU | 2412203 C | 2/2011 |
| WO | 1996/02641 A | 2/1996 |
| WO | 2001/74405 A | 10/2001 |
| WO | 2002/16620 A | 2/2002 |
| WO | 2002/055705 A | 7/2002 |
| WO | 2002/086443 A | 10/2002 |
| WO | 2002/088081 A | 11/2002 |
| WO | 2002/092635 A | 11/2002 |
| WO | 2003/004045 A | 1/2003 |
| WO | 2004/020668 A | 3/2004 |
| WO | 2004/031413 A | 4/2004 |
| WO | 2005/004912 A | 1/2005 |
| WO | 2006/013733 A | 2/2006 |
| WO | 2006/085684 A | 8/2006 |
| WO | 2007/053577 A | 5/2007 |
| WO | 2007/148417 A | 12/2007 |
| WO | 2013/025446 A2 | 2/2013 |
| WO | 2013/157410 A1 | 10/2013 |

OTHER PUBLICATIONS

Malia et al., Proteins, 2016; 84:427-434. (Year: 2016).*
Barthelemy et al., Journal of Biological Chemistry, 2008, 283:3639-3654. (Year: 2008).*
Beiboer et al., Journal of Molecular Biology, 2000, 296:833-849. (Year: 2000).*
Choi et al., 2011, Molecular BioSystems, 2011, 7:3327-334. (Year: 2011).*
De Genst et al., Developmental and Comparative Immunology, 2006, 30:187-98. (Year: 2006).*
Griffiths et al., The EMBO Journal, 1993, 12:725-734. (Year: 1993).*
Klimka et al., British Journal of Cancer, 2000, 83:252-260. (Year: 2000).*
Ward et al., Nature, 1989, 341:544-546. (Year: 1989).*
Raman et al, PNAS (2019) vol. 116 No. 14, 6812-6817 (Year: 2019).*
Dann, et al; Insights into Wnt binding and signaling from the structures of two Frizzled cysteine-rich domains; Nature; Jul. 5, 2001; 412(6842):86-90.
Fukukawa, et al; Functional analysis of FZD10, an up-regulated gene in synovial sarcoma, and therapeutic potential of its antibody; Proceedings of the 63rd Annual Meeting of the Japanese Cancer Assoc.; 2004; 63:82. W-148.
Fukukawa, et al; Activation of the non-canonical Dvl-Rac1-JNK pathway by Frizzled homologue 10 in human synovial sarcoma; Oncogene; Feb. 26, 2009; 28(8):1110-20.

(Continued)

Primary Examiner — Julie Wu
Assistant Examiner — Cheom-Gil Cheong
(74) Attorney, Agent, or Firm — Kilpatrick Townsend & Stockton LLP

(57) ABSTRACT

The present invention relates to monoclonal antibodies against FZD10. Furthermore, the present invention provides methods for diagnosing FZD10-related diseases using such an antibody, methods for detecting a FZD10 protein, methods for determining drug efficacy after treatment with FZD10 inhibitors, and methods of screening for subjects in whom treatment with FZD10 inhibitors is highly effective, and provides diagnostic reagents containing such an antibody.

16 Claims, 4 Drawing Sheets

Specification includes a Sequence Listing.

(56) References Cited

OTHER PUBLICATIONS

Fukukawa, et al; Therapeutic potential of antibodies against frizzled homologue 10, a cell-surface protein, for synovial sarcoma; Proc Amer Assoc Cancer Res.; vol. 47, 2006. Abstract # 1975.
Fukukawa, et al; Radioimmunotherapy of human synovial sarcoma using a monoclonal antibody against FZD10; Proceedings of the 66$^{th}$ Annual Meeting of the Japanese Cancer Assoc.; 2007; 66:69. EW11-4.
Fukukawa, et al; Functional analysis of FZD10, an up-regulated gene in synovial sarcoma, and therapeutic potential of its antibody; Proceedings of the 64$^{th}$ Annual Meeting of the Japanese Cancer Assoc.; 2005; 64:54. W-093.
Fukukawa, et al; Therapeutic potential of antibodies against FZD10, a cell-surface protein, for synovial sarcomas; Proc Amer Assoc Cancer Res; vol. 46; 2005; 165; #702.
Fukukawa, et al; Radioimmunotherapy of human synovial sarcoma using a monoclonal antibody against FZD10; Cancer Sci.; Feb. 2008; 99(2):432-40.
Hanaoka, et al; Radioimmunotherapy of solid tumors targeting a cell-surface protein, FZD10: therapeutic efficacy largely depends on radiosensitivity; Ann Nucl Med.; Jul. 2009; 23(5):479-85.
Kamarainen, et al; Epithelial Expression of Glycodelin in Biphasic Synovial Sarcomas; Int. J Cancer; May 18, 1998; 76(4):487-90.
Katagiri, et al; The development of anti-FZD10 antibody for molecular target therapy in synovial sarcoma; 3$^{RD}$ Japanese Cancer Assoc. Conference; 2006; 3:35. O-26.
Kirikoshi, et al; Expression profiles of 10 members of Frizzled gene family in human gastric cancer; Int. J Oncol.; Oct. 2001; 19(4):767-71.
Koike, et al; Molecular Cloning of Frizzled-10, a Novel Member of the Frizzled Gene Family; Biochem Biophys Res Commun.; Aug. 19, 1999; 262(1):39-43.
Nagayama, et al; Genome-wide Analysis of Gene Expression in Synovial Sarcomas Using a cDNA Microarray; Cancer Res.; Oct. 15, 2002; 62(20):5859-66.
Nagayama, et al; Therapeutic potential of antibodies against FZD10, a cell-surface protein, for synovial sarcomas; Oncogene; Sep. 15, 2005; 24(41):6102-12.
Nagayama, et al; The therapeutic potential of antibodies against cell-surface protein, FZD10, for Synovial saromas; Proceedings of the 62$^{nd}$ Meeting of the Japanese Cancer Assoc.; 2003; 62:112. 1171-OP.
Nagayama, et al; A novel molecular classification of soft tissue sarcomas based on expression profiles by means of a genome-wide cDNA microarray analysis; Proceedings of the the 63$^{rd}$ Meeting of the Japanese Cancer Assoc.; 2004; 63:82. W-149.
Nagayama, et al; Gene Expression Profiles of Synovial Sarcoma; Proceedings of the 35$^{th}$ Annual Musculoskeletal Tumor Meeting of the Japanese Orthopaedic Assoc.; J. Jpn. Orthop. Assoc.; 76(6) 2002:S735. I-3-P3-5.
Tamborini, et al; c-KIT and c-KIT ligand (SCF) in synovial sarcoma (SS): an mRNA expression analysis in 23 cases; Br J Cancer; Aug. 3, 2001; 85(3):405-11.
Terasaki, et al; Frizzled-10, up-regulated in primary colorectal cancer, is a positive regulator of the WNT-β-catenin—TCF signaling pathway; Int J Mol Med.; Feb. 2002; 9(2): 107-12.
Yamada, et al; Immunohistochemical study of FZD10 expression in colon adenomas, primary colorectal cancers and metastatic liver lesions; Proceedings of the 66$^{th}$ Annual Meeting of the Japanese Cancer Assoc; 2007; 66:227. P-1379.
Japan Patent Office; International Search Report of PCT/JP2017/036081 dated Nov. 14, 2017.
Roitt, et al; Enzymatic degradation of human IgG1; Immunology; Moscow: Mir., 2000: 110-1.
Tarantul; Russian-English Bioengineering Explanatory Dictionary; Languages of Slavic Cultures; Moscow; 2009: 72.

* cited by examiner

MONOCLONAL ANTIBODY AGAINST FZD10 AND USE THEREOF

CROSS-REFERENCE TO RELATED APPLICATIONS

The present application is a § 371 National Phase Application of PCT/JP2017/036081, filed Oct. 4, 2017, which application claims the benefit of Japanese Patent Application No. JP 2016-197881, filed Oct. 6, 2016, the entire contents of which are incorporated by reference in their entireties for all purposes herein.

TECHNICAL FIELD

The present invention relates to monoclonal antibodies against FZD10, methods for diagnosing FZD10-related diseases using such an antibody, methods for detecting a FZD10 protein, methods for determining drug efficacy after treatment with a FZD10 inhibitor, methods of screening for subjects in whom treatment with a FZD10 inhibitor is highly effective, and diagnostic reagents containing such an antibody.

BACKGROUND ART

Frizzled proteins are a family of G-protein coupled receptors that have a binding site for Wnt protein ligands. Gene analyses have identified 18 Wnt genes and ten Frizzled genes (FZD1 to FZD10) so far, and these are known to be all structurally highly similar.

Frizzled proteins are seven-transmembrane proteins which have an extracellular cysteine-rich domain at the N terminus. This cysteine rich domain is the binding site for Wnt ligands. The binding between Wnt ligands and Frizzled receptors is not necessarily one to one. It has been found that one Wnt ligand binds to multiple Frizzled receptors, and multiple Wnt ligands to one Frizzled receptor.

It is said that binding between a Wnt ligand and a Frizzled receptor activates a Wnt signaling pathway. There are a number of Wnt signaling pathways that either activate the β-catenin pathway or do not involve β-catenin, and it is considered that different Wnt ligand/Frizzled receptor combinations activate different pathways.

The Wnt/β-catenin signaling pathway activated upon receptor binding is mediated by the cytoplasmic protein Dishevelled (Dsh) interacting directly with the Frizzled receptor and results in the cytoplasmic stabilization and accumulation of β-catenin in the cytoplasm. In the absence of a Wnt signal, β-catenin is localized to a cytoplasmic destruction complex including the tumor suppressor proteins adenomatous polyposis coli (APC) and Axin. These proteins function as critical scaffolds for glycogen synthase kinase (GSK)-3β to bind and phosphorylate β-catenin, marking it for degradation via the ubiquitin-proteasome pathway (Patent Document 1). The β-catenin-independent pathway has been shown to participate in a number of processes which include planar cellular polarity (PCP) involved in regulation of the cytoskeletal system, Wnt/$Ca^{2+}$ pathway involved in cell motility and adhesion, and pathways involved in regulation of myogenesis via protein kinase A. Frizzled receptors can be dimerized, and this dimerization has been reported to be involved in activation of the Wnt signaling pathway (Non-patent Document 1).

FZD10 (reference sequence: Genbank Accession Number NM_007197.3 (SEQ ID NO:21)) mRNA has been reported to be upregulated in many cancer cell lines including cell lines of the cervical region, digestive tract, and glioblastoma, and in approximately 40% of primary stomach cancer and primary colon cancer, and most synovial sarcoma tissues (Patent Documents 1 and 2, and Non-patent Documents 2 and 3). Examples of diseases relating to overexpression of the FZD10 protein include synovial sarcoma, colorectal cancer (large intestine cancer), stomach cancer, chronic myeloid leukemia (CML), and acute myeloid leukemia (AML) (Patent Documents 3 to 5). Therefore, FZD10 is considered to be an appropriate target for anticancer agents, and FZD10-specific siRNAs have been shown to suppress proliferation of synovial sarcoma cells, and antibodies against FZD10 have been shown to have antitumor activity in a mouse graft model of synovial sarcoma (Patent Documents 3 and 4). Furthermore, monoclonal antibodies against FZD10 may be predicted to be useful as diagnostic agents in therapies. In addition to successful cases of clinical application of monoclonal antibodies, such as diagnostic agents for trastuzumab, rituximab, and bevacizumab against breast cancer, malignant lymphoma, and colon cancer, development of several monoclonal antibodies against other molecular targets is ongoing, and their diagnostic effects are being evaluated. From the viewpoint of selecting patients effectively responding to therapeutic agents, these diagnostic agents are expected to lead to more effective therapies.

PRIOR ART DOCUMENTS

Patent Documents

[Patent Document 1] WO2007/053577
[Patent Document 2] WO2004/020668
[Patent Document 3] WO2005/004912
[Patent Document 4] WO2006/013733
[Patent Document 5] WO2007/148417

Non-Patent Documents

[Non-patent Document 1] Charles E. Dann et al., Nature (2001), 412:86-90
[Non-patent Document 2] H. Terasaki et al., Int. J. Mol. Med. (2002) 9, 107-112
[Non-patent Document 3] S. Nagayama et al., Oncogene (2005) 24, 6201-6212

SUMMARY OF THE INVENTION

Problems to be Solved by the Invention

In treatment of tumor using a molecular target drug, it is important for a diagnostic agent to detect a cell protein that is overexpressed in the most part of the target tumor and not expressed or only minimally expressed in normal tissues. However, specific, highly sensitive detection of a protein expressed in tumors is difficult, and antibodies against such a protein are also difficult to obtain. For example, for FZD10, which is considered to be a target for anticancer agents, several antibodies are commercially available. However, when commercially-available antibodies obtained by the present inventors were used to stain FZD10-expressing cells, even cells with low FZD10 expression levels sometimes gave a positive signal (false positive). Thus, there is a concern that antibodies with insufficient immunological specificity might not allow different FZD10 expression levels to be clearly detected using the intensity of antibody reaction as an indicator. Therefore, an objective of the present invention is to provide antibodies that bind to FZD10 with specificity and high sensitivity.

Means for Solving the Problems

Accordingly, the present inventors searched for antibodies that bind specifically to FZD10 from among monoclonal antibodies obtained by immunizing mice with a FZD10 antigen, and succeeded in identifying a particular antibody clone which can specifically bind to a recombinant human FZD10 protein and can specifically detect a FZD10 protein expressed in cells and tissues.

Specifically, the present invention relates to the following:

[1] an antibody or antigen-binding fragment thereof capable of binding to a FZD10 protein or a partial peptide thereof, which comprises either or both of:

a heavy chain variable region comprising
CDR1 comprising the amino acid sequence of SEQ ID NO: 1,
CDR2 comprising the amino acid sequence of SEQ ID NO: 2, and
CDR3 comprising the amino acid sequence of SEQ ID NO: 3; and
a light chain variable region comprising
CDR1 comprising the amino acid sequence of SEQ ID NO: 4,
CDR2 comprising the amino acid sequence of SEQ ID NO: 5, and
CDR3 comprising the amino acid sequence of SEQ ID NO: 6;

[2] the antibody or antigen-binding fragment thereof of [1], which comprises either or both of a heavy chain variable region comprising the amino acid sequence of SEQ ID NO: 7 and a light chain variable region comprising the amino acid sequence of SEQ ID NO: 8;

[3] the antibody or antigen-binding fragment thereof of [1] or [2], which specifically recognizes a polypeptide consisting of the amino acid sequence of SEQ ID NO: 9;

[4] an antibody or antigen-binding fragment thereof, which competes with the antibody of any one of [1] to [3] for specific binding to FZD10;

[5] the antibody or antigen-binding fragment thereof of any one of [1] to [4], which is conjugated with an affinity label, an enzyme label, a radioisotope label, or a fluorescent label;

[6] a polynucleotide encoding the antibody or antigen-binding fragment thereof of any one of [1] to [5];

[7] a reagent for diagnosing a FZD10-related disease, determining drug efficacy after treatment with a FZD10 inhibitor, or screening for a subject in whom treatment with a FZD10 inhibitor is highly effective, wherein the reagent comprises the antibody or antigen-binding fragment thereof of any one of [1] to [5];

[8] a method for diagnosing a FZD10-related disease or a predisposition for developing the disease in a subject, comprising the steps of:

(a) contacting a sample isolated from the subject with the antibody or antigen-binding fragment thereof of any one of [1] to [5];

(b) detecting a FZD10 protein in the sample by detecting binding between the antibody or antigen-binding fragment thereof and the sample; and (c) comparing the level of the FZD10 protein in the sample to a control, wherein a higher FZD10 protein level than the control indicates that the subject suffers from the disease or has a risk of developing the disease; [9] the reagent of [7] or the method of [8], wherein the FZD10-related disease is a cancer expressing FZD10;

[10] the reagent or method of [9], wherein the cancer is selected from the group consisting of synovial sarcoma, lung cancer, esophageal cancer, colorectal cancer (large intestine cancer), stomach cancer, chronic myeloid leukemia (CML), and acute myeloid leukemia (AML);

[11] a method for detecting a FZD10 protein in a sample, comprising the steps of:

(a) contacting a sample isolated from a subject with the antibody or antigen-binding fragment thereof of any one of [1] to [5]; and (b) detecting a FZD10 protein in the sample by detecting binding between the antibody or antigen-binding fragment thereof and the sample;

[12] a method for determining drug efficacy after treatment with a FZD10 inhibitor in a subject, comprising the steps of:

(a) contacting a sample isolated from the subject with the antibody or antigen-binding fragment thereof of any one of [1] to [5];

(b) detecting a FZD10 protein in the sample by detecting binding between the antibody or antigen-binding fragment thereof and the sample; and (c) comparing the level of the FZD10 protein in the sample to the expression level before administration of the drug, wherein a FZD10 protein level lower than that before administration of the drug indicates that the drug has been effective in the subject;

[13] a method of screening for a subject in whom treatment with a FZD10 inhibitor is highly effective, comprising the steps of:

(a) contacting a sample isolated from the subject with the antibody or antigen-binding fragment thereof of any one of [1] to [5];

(b) detecting a FZD10 protein in the sample by detecting binding between the antibody or antigen-binding fragment thereof and the sample; and (c) comparing the FZD10 protein level in the sample to a control, wherein the FZD10 protein level equal to or higher than the control indicates that treatment with a FZD10 inhibitor is highly effective in the subject;

[14] the method of any one of [8] to [13], wherein the sample is a cell or tissue isolated from the subject;

[15] a method for producing an antibody that can bind to a FZD10 protein or a partial peptide thereof, comprising the steps of:

(a) culturing a cell comprising a vector inserted with the polynucleotide of [6]; and (b) collecting the antibody from a culture or culture medium of the cell.

The present invention further relates to the following:

[16] a method for detecting a diagnostic marker for a FZD10-related disease or a predisposition for developing the disease, comprising the steps of:

(a) contacting a sample isolated from the subject with the antibody or antigen-binding fragment thereof of any one of [1] to [5]; and (b) detecting a FZD10 protein in the sample as the marker by detecting binding between the antibody or antigen-binding fragment thereof and the sample;

[17] the antibody or antigen-binding fragment thereof of any one of [1] to [5] for use in diagnosing a FZD10-related disease or a predisposition for developing the disease;

[18] use of the antibody or antigen-binding fragment thereof of any one of [1] to [5] in manufacture of a reagent for diagnosing a FZD10-related disease or a predisposition for developing the disease;

[19] a method for detecting a drug efficacy marker for a FZD10 inhibitor, comprising the steps of:

(a) contacting a sample isolated from the subject with the antibody or antigen-binding fragment thereof of any one of [1] to [5]; and (b) detecting a FZD10 protein in the sample as the marker by detecting binding between the antibody or antigen-binding fragment thereof and the sample;

[20] the antibody or antigen-binding fragment thereof of any one of [1] to [5] for use in determining drug efficacy after treatment with a FZD10 inhibitor;

[21] use of the antibody or antigen-binding fragment thereof of any one of [1] to [5] in manufacture of a reagent for determining drug efficacy after treatment with a FZD10 inhibitor;

[22] a method for detecting a FZD10 inhibitor treatment responsiveness marker, comprising the steps of:

(a) contacting a sample isolated from the subject with the antibody or antigen-binding fragment thereof of any one of [1] to [5]; and (b) detecting a FZD10 protein in the sample as the marker by detecting binding between the antibody or antigen-binding fragment thereof and the sample;

[23] the antibody or antigen-binding fragment thereof of any one of [1] to [5], which is for use in screening for a subject in whom treatment with a FZD10 inhibitor is highly effective; and

[24] use of the antibody or antigen-binding fragment thereof of any one of [1] to [5] in manufacture of a reagent for screening for a subject in whom treatment with a FZD10 inhibitor is highly effective.

In addition to the above, other objects and features of the present invention will become more fully apparent when the following detailed description is read in conjunction with the accompanying figures and examples. However, it is to be understood that both the foregoing summary of the present invention and the following detailed description are of exemplified embodiments, and not restrictive of the present invention or other alternate embodiments of the present invention. In particular, while the present invention is described herein with reference to a number of specific embodiments, it will be appreciated that the description is illustrative of the present invention and is not constructed as limiting of the present invention. Various modifications and applications may occur to those who are skilled in the art, without departing from the spirit and the scope of the present invention, as described by the appended claims. Likewise, other objects, features, benefits and advantages of the present invention will be apparent from this summary and certain embodiments described below, and will be readily apparent to those skilled in the art. Such objects, features, benefits and advantages will be apparent from the above in conjunction with the accompanying examples, data, figures and all reasonable inferences to be drawn therefrom, alone or with consideration of the references incorporated herein.

DESCRIPTION OF EMBODIMENTS

Figure 1:
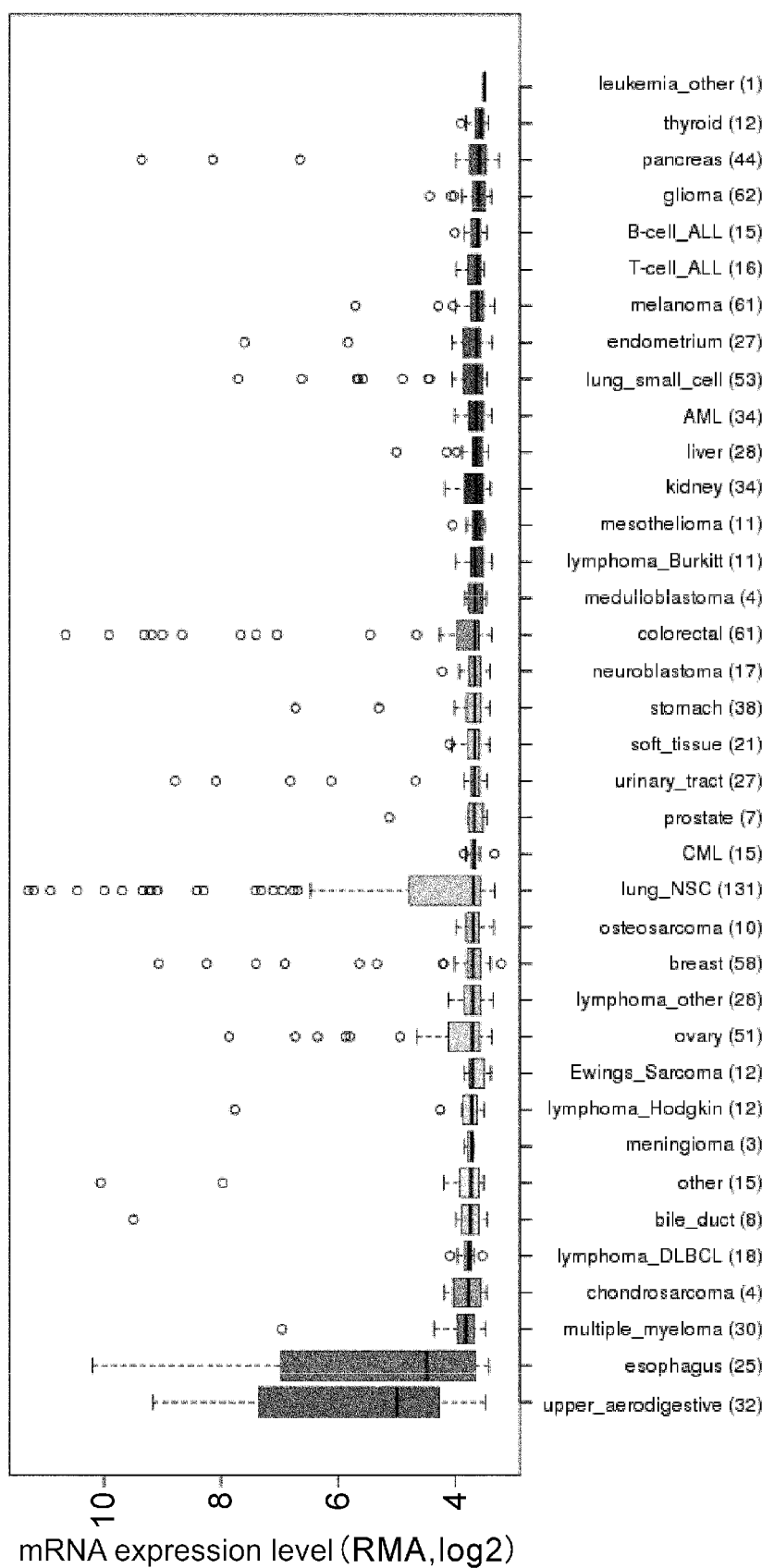
FIG. 1 shows the expression of FZD10 mRNA in cell lines of each cancer type in the Cancer Cell Line Encyclopedia (CCLE), which is an mRNA expression analysis database using cell lines of each cancer type.

Although any methods and materials similar or equivalent to those described herein can be used in the practice or testing of embodiments of the present invention, the preferred methods, devices, and materials are now described. However, before the present materials and methods are described, it is to be understood that the present invention is not limited to the particular sizes, shapes, dimensions, materials, methodologies, protocols, etc. described herein, as these may vary in accordance with routine experimentation and optimization. It is also to be understood that the terminology used in the description is for the purpose of describing the particular versions or embodiments only, and is not intended to limit the scope of the present invention which will be limited only by the appended claims.

The present invention provides anti-FZD10 monoclonal antibodies that can specifically bind to a FZD10 protein or a partial peptide thereof. The present invention provides evidence that an anti-FZD10 monoclonal antibody of the present invention has high specificity in detecting a FZD10 protein in immunohistochemical staining.

The anti-FZD10 antibody (10A8H4G4) of the present invention has at least the following amino acid sequences in the variable regions:

```
10A8H4G4, Heavy chain variable region amino acid
sequence (excluding the signal sequence):
                                        (SEQ ID NO: 7)
QVTLKESGPGILQPSQTLSLTCSFSGFSLSTSGLGVSWIRQPSGKGLE

WLAHIYWDDDKRYNPSLKSRLTISKDTSSNQVFLKITSVDTADTATYY

CARRAYYGNYYALDYWGQGTSVTVSS;

10A8H4G4, Light chain variable region amino acid
sequence (excluding the signal sequence):
                                        (SEQ ID NO: 8)
DIVMTQSPSSLTVTAGEKVTMSCKSSQSLLNSGNQKNYLTWYQQKPGQ

PPKLLIYWASTRKSGVPDRFTGSGSGTDFTLTISSVQAEDLAVYYCQN

DYSYPVTFGAGTKLELKRAD.
```

The antibodies of the present invention can be produced by recombinant techniques using DNAs that encode the aforementioned amino acid sequences.

The antibodies of the present invention were obtained by screening and selecting antibodies binding with FZD10 by ELISA from among multiple antibody-producing hybridomas obtained by immunization of mice. Antibodies selected by ELISA were subjected to further selection by immunological staining. Antibodies by which forced-expression cells (positive control cells) were indicated as positive and negative control cells as negative were selected. Among the selected antibodies, those by which endogenous FZD10-expressing cells (positive control cells) were indicated as positive and negative control cells as negative were further selected. If the interaction with FZD10 is not very strong, antibodies having weak binding ability will follow around as background. Therefore, the screening was performed by immunological staining using a cell line whose endogenous FZD10 expression level had been determined in advance. In this manner, an antibody of interest having strong binding ability to FZD10 was successfully selected.

The antibodies of the present invention specifically bind to FZD10. Therefore, the antibodies of the present invention are useful as tools for detecting FZD10 or FZD10-expressing cells or tissues. Furthermore, the antibodies of the present invention can be conjugated with a label that may be used to detect the antibodies, and such labeled antibodies are more preferred for detection of FZD10-expressing cancer cells or cancer tissues, such as colorectal cancer. The label to be conjugated with the antibodies of the present invention may be any label as long as it can detect an antibody bound to FZD10, and include affinity labels (for example, biotin and avidin), enzyme labels (for example, horseradish peroxidase, and alkaline phosphatase), and fluorescent labels (for example, FITC and rhodamine).

When the antibodies of the present invention are used as diagnostic agents to select cancer therapy patients, the antibodies of the present invention may be directly used or prepared as a composition suitable for various types of usage.

I. Definitions

The words "a", "an", and "the" as used herein mean "at least one" unless otherwise specifically indicated.

The terms "isolated" and "purified" used in relation with a substance (for example, peptide, antibody, polynucleotide or such) indicate that the substance does not substantially contain at least one substance that may else be included in a natural source. Thus, an isolated or purified antibody refers to an antibody that does not substantially contain another cellular material, for example, carbohydrate, lipid and other contaminating proteins from the cell or tissue source from which the antibody is derived. In a preferred embodiment, the antibodies of the present invention are isolated or purified.

The terms "polypeptide" and "protein" are used interchangeably herein, and refer to polymers of amino acid residues. These terms are applied to naturally occurring amino acid polymers and also to non-naturally occurring amino acid polymers comprising one or more non-naturally occurring amino acid residues. Non-naturally occurring amino acids include amino acid analogs, amino acid mimetics, and such.

The terms "polynucleotide", "oligonucleotide", and "nucleic acid" are used interchangeably herein, and refer to a polymer of nucleotides.

Unless otherwise specified, the term "FZD10-related disease" means a cancer expressing FZD10.

Unless otherwise specified, the term "cancer" refers to cancer expressing FZD10, and preferably cancer overexpressing the FZD10 gene, and its examples include, but are not limited to, synovial sarcoma, lung cancer, esophageal cancer, colorectal cancer (large intestine cancer), stomach cancer, chronic myeloid leukemia (CML), and acute myeloid leukemia (AML). For example, it is possible to know what cancer cells express FZD10 by use of the Cancer Cell Line Encyclopedia (CCLE), which is a database of mRNA expression analyses using cell lines of each cancer type. The present application has also found remarkable upregulation in lung cancer, esophageal cancer, and colorectal cancer (large intestine cancer) (FIG. 1).

The term "antibody" as used herein is intended to include immunoglobulins and fragments thereof which are specifically reactive to the designated protein or peptide thereof. An antibody can include antibodies fused to other proteins or labels, and antibody fragments. Furthermore, an antibody herein is used in the broadest sense and specifically covers intact monoclonal antibodies, polyclonal antibodies, multispecific antibodies (e.g. bispecific antibodies) formed from at least two intact antibodies, and antibody fragments so long as they exhibit the desired biological activity. An "antibody" indicates all classes (e.g. IgA, IgD, IgE, IgG and IgM).

"Antibody fragments" is a part of an intact antibody, generally comprises one or more antigen binding regions or variable regions of the intact antibody. Therefore, in the present invention, antibody fragments may comprise one or more antigen binding portions of the intact antibody. The term "antigen-binding portion" or "antigen-binding fragment" of an antibody, as used herein, refers to one or more immunological active fragments of an antibody that retain the ability to specifically bind to an antigen (e.g., FZD10). It has been shown that the antigen-binding function of an antibody can be performed by fragments of a full-length antibody. Examples of antibody fragments include Fab, Fab', F(ab')2, and Fv fragments; linear antibodies; and single chain antibody molecules. Regardless of structure, an antibody fragment binds to the same antigen as that recognized by the intact antibody. The term "antibody fragment" also includes a synthetic or a genetically engineered polypeptide that binds to a specific antigen, such as polypeptides consisting of the light chain variable region, "Fv" fragments consisting of the variable regions of the heavy and light chains, recombinant single chain polypeptide molecules in which light and heavy variable regions are connected by a peptide linker ("scFv proteins"), and minimal recognition units consisting of the amino acid residues that imitate the hypervariable region.

Unless otherwise specified, the technical terms and scientific terms used herein all have the same meanings as terms commonly understood by one of ordinary skill in the art to which the present invention belongs.

In the present invention, the specific binding of an antibody with a FZD10 protein can be evaluated, for example, by competition between antibodies. Specifically, the specificity of a candidate antibody can be evaluated using an antibody of the present invention, for example, an antibody comprising a heavy chain variable region comprising the amino acid sequence of SEQ ID NO: 7 and a light chain variable region comprising the amino acid sequence of SEQ ID NO: 8, as a reference antibody. A representative reference antibody is 10A8H4G4. If the candidate antibody competes against the antigen-antibody reaction between the reference antibody and the human FZD10 protein, the candidate antibody can be confirmed to have specificity equivalent to that of the reference antibody. For example, occurrence of competition between the antibodies can be determined if the amount of the reference antibody binding to the FZD10 protein in the absence of the candidate antibody is inhibited by 10%, 20%, 30% or 40%, or more preferably 50% or more when the reference antibody and the FZD10 protein are reacted in the presence of the candidate antibody. Competition between antibodies can be evaluated using not only FZD10 protein but also a partial peptide thereof as long as the reference antibody can bind to it. A preferred partial peptide is an N-terminal extracellular domain peptide of FZD10 protein, for example, a partial peptide comprising the amino acid sequence of SEQ ID NO: 9.

II. Production of Antibodies

The present invention uses anti-FZD10 monoclonal antibodies. The antibodies will be provided by methods well known in the art.

Exemplary techniques for the production of the antibodies used in accordance with the present invention are described below.

(i) Monoclonal Antibodies

Monoclonal antibodies are obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies.

For example, the monoclonal antibodies may be made using the hybridoma method first described by Kohler et al., Nature, 256: 495 (1975), or may be made by recombinant DNA methods (U.S. Pat. No. 4,816,567).

In the hybridoma method, a mouse or other appropriate host animal, such as a hamster, is immunized with a FZD10 polypeptide (a FZD10 protein or a partial polypeptide thereof) to elicit lymphocytes that produce or are capable of producing antibodies that will specifically bind to FZD10 polypeptides. Alternatively, lymphocytes may be immunized with a FZD10 polypeptide in vitro. Lymphocytes then are fused with myeloma cells using a suitable fusing agent, such as polyethylene glycol, to form a hybridoma cell (Goding, Monoclonal Antibodies: Principles and Practice, pp. 59-103 (Academic Press, 1986)).

The hybridoma cells prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas can typically include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Preferred myeloma cell lines include murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Manassas, Va., USA. Human myeloma and mouse-human heteromyeloma cell lines also have been described for the production of human monoclonal antibodies (Kozbor, J. Immunol., 133: 300 1 (1984); Brodeur et al., Monoclonal Antibody Production Techniques and Applications, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the 30 Scatchard analysis of Munson et al., Anal. Biochem., 107: 220 (1980).

After hybridoma cells are identified that produce antibodies of the desired specificity, affinity, and/or activity, the clones may be subcloned by limiting dilution procedures and grown by standard methods (Goding, Monoclonal Antibodies: Principles and Practice, pp. 59-103 (Academic Press, 1986)). Suitable culture media for this purpose include, for example, D-MEM or RPML-1640 medium. In addition, the hybridoma cells may be grown in vivo as ascites tumors in an animal.

Monoclonal antibodies secreted by subclones may be purified to homogeneity. For example, antibody separation and purification can be performed according to separation methods and purification methods used for general proteins. For example, an antibody can be appropriately separated and isolated from a culture medium, ascites, or blood serum by appropriately selecting and combining use of column chromatographies such as affinity chromatography, filter, ultra-filtration, salting-out, dialysis, SDS-polyacrylamide gel electrophoresis and isoelectric focusing electrophoresis (Antibodies: A Laboratory Manual. Ed Harlow and David Lane, Cold Spring Harbor Laboratory (1988)), but are not limited thereto. Protein A column and protein G column can be used as the affinity column. Exemplary protein A columns to be used include, for example, Hyper D, POROS and Sepharose F.F. (Pharmacia).

Besides affinity chromatography, exemplary chromatography includes, for example, ion-exchange chromatography, hydrophobic chromatography, gel filtration, reversed-phase chromatography, adsorption chromatography and such (Strategies for Protein Purification and Characterization: A Laboratory Course Manual. Ed Daniel R. Marshak et al., Cold Spring Harbor Laboratory Press (1996)). The chromatography procedures can be carried out by liquid-phase chromatography such as HPLC and FPLC.

DNAs encoding the monoclonal antibodies are readily isolated and sequenced using conventional procedures (e.g., by using oligonucleotide probes that are capable of binding specifically to genes encoding the heavy and light chains of murine antibodies). The hybridoma cells serve as a preferred source of such DNAs. Once isolated, the DNAs may be placed into expression vectors, which are then transfected into host cells such as E. coli cells, simian COS cells, Chinese Hamster Ovary (CHO) cells, or myeloma cells that do not otherwise produce immunoglobulin protein, to obtain the synthesis of monoclonal antibodies in the recombinant host cells. Review articles on recombinant expression in bacteria of DNAs encoding the antibody include Skerra et al., Curr. Opinion in Immunol., 5: 256-262 (1993) and Pluckthun, Immunol. Revs., 130: 151-188 (1992).

Another method of generating specific antibodies, or antibody fragments, reactive against a FZD10 is to screen expression libraries encoding immunoglobulin genes, or portions thereof, expressed in bacteria with a FZD10 protein or a partial peptide thereof. For example, complete Fab fragments, VH regions and Fv regions can be expressed in bacteria using phage expression libraries. See for example, Ward et al., Nature 341: 544-546 (1989); Huse et al., Science 246: 1275-1281 (1989); and McCafferty et al., Nature 348: 552-554 (1990). Screening such libraries with, for example, a FZD10 peptide, can identify immunoglobulin fragments reactive with FZD10. Alternatively, the SCID-hu mouse (available from Genpharm) can be used to produce antibodies or fragments thereof.

In a further embodiment, antibodies or antibody fragments can be isolated from antibody phage libraries generated using the techniques described in McCafferty et al., Nature, 348: 552-554 (1990). Clackson et al., Nature, 352: 624-628 (1991) and Marks et al., J MoL BioL, 222: 581-597 (1991) describe the isolation of murine and human antibodies, respectively, using phage libraries. Subsequent publications describe the production of high affinity (nM range) human antibodies by chain shuffling (Marks et al., BioTechnology, 10: 779-783 (1992)), as well as combinatorial infection and in vivo recombination as a strategy for constructing very large phage libraries (Waterhouse et al., Nuc. Acids. Res., 21: 2265-2266 (1993)). Thus, these techniques are viable alternatives to traditional monoclonal antibody hybridoma techniques for isolation of monoclonal antibodies.

The present invention provides antibodies suitable for diagnosing FZD10-related diseases, determining drug efficacy after treatment with a FZD10 inhibitor, and screening for subjects in whom treatment with a FZD10 inhibitor is highly effective. The present invention successfully established a mouse monoclonal antibody clone (10A8H4G4) that can detect a FZD10 protein with high specificity in immunohistochemical staining and flow cytometry. It was demonstrated that this antibody clone, when used for immunohistochemical staining of clinical lung cancer specimens, gave positive results in lung cancer specimens which had been confirmed to express FZD10 at high levels by real-time PCR, but little staining in lung cancer specimens which had been confirmed to express FZD10 at low levels by real-time PCR. Furthermore, whereas commercially available anti-FZD10 antibodies stained both a sample produced from a cell line forced to express FZD10 and a sample produced from a non-FZD10-expressing cell line, the anti-FZD10 antibody of the present invention was shown to specifically stain the sample produced from the cell line forced to express FZD10. The antibodies of the present invention, which have such high antigen specificity, are advantageous in selecting patients with high FZD10 expression levels, and also in selecting patients in whom treatment with a FZD10 inhibitor is likely to be effective.

The amino acid sequences of the heavy chain variable region (H chain V region) and the light chain variable region (L chain V region) of the anti-FZD10 mouse monoclonal antibody clone of the present invention (10A8H4G4) are shown in SEQ ID NOs: 7 and 8, respectively.

The complementarity determining regions (CDRs) included in a heavy chain variable region and a light chain variable region can be determined according to methods well known in the art. For example, the method described by Kabat et al. (Kabat E. A. et al. (1991) Sequence of Proteins of Immunological Interest. 5th Edition) or Chothia et al. (Chothia et al. J. Mol. Biol. (1987) 196; 901-917) is generally used for CDR determination. CDRs 1, 2, and 3 of the heavy chain variable region of the anti-FZD10 mouse monoclonal antibody clone of the present invention (10A8H4G4) as determined according to Kabat's definition are shown in SEQ ID NOs: 1, 2, and 3, respectively, and CDRs 1, 2, and 3 of the light chain variable region of this clone are shown in SEQ ID NOs: 4, 5, and 6, respectively.

Therefore, the present invention provides antibodies or antigen-binding fragments thereof capable of binding to a FZD10 protein or a partial peptide thereof, which comprise either one or both of a heavy chain variable region and a light chain variable region, wherein the heavy chain variable region comprises:

CDR1 comprising the amino acid sequence of SEQ ID NO: 1,

CDR2 comprising the amino acid sequence of SEQ ID NO: 2, and

CDR3 comprising the amino acid sequence of SEQ ID NO: 3;

and the light chain variable region comprises:

CDR1 comprising the amino acid sequence of SEQ ID NO: 4,

CDR2 comprising the amino acid sequence of SEQ ID NO: 5, and

CDR3 comprising the amino acid sequence of SEQ ID NO: 6.

In the present invention, a partial peptide of FZD10 protein to which the antibodies of the present invention bind is preferably an N-terminal extracellular domain peptide of the FZD10 protein, which consists of, for example, an amino acid sequence that contains the amino acid sequence (SEQ ID NO: 9) corresponding to positions 21 to 161 of the FZD10 protein (SEQ ID NO: 22) and is selected from within SEQ ID NO: 22. More preferably, the partial peptide of the FZD10 protein in the present invention may consist of the amino acid sequence of SEQ ID NO: 9.

An example of the above-mentioned heavy chain variable region comprising "CDR1 comprising the amino acid sequence of SEQ ID NO: 1; CDR2 comprising the amino acid sequence of SEQ ID NO: 2; and CDR3 comprising the amino acid sequence of SEQ ID NO: 3" is a heavy chain variable region comprising the amino acid sequence of SEQ ID NO: 7. An example of the above-mentioned light chain variable region comprising "CDR1 comprising the amino acid sequence of SEQ ID NO: 4; CDR2 comprising the amino acid sequence of SEQ ID NO: 5; and CDR3 comprising the amino acid sequence of SEQ ID NO: 6" is a light chain variable region comprising the amino acid sequence of SEQ ID NO: 8.

Therefore, in one embodiment, the present invention provides antibodies or antigen-binding fragments thereof, which comprise either one or both of a heavy chain variable region comprising the amino acid sequence of SEQ ID NO: 7 and a light chain variable region comprising the amino acid sequence of SEQ ID NO: 8.

The antibodies of the present invention can be prepared by conventional methods. For example, the antibody may be prepared by integrating a polynucleotide encoding the antibody polypeptide into a suitable vector, introducing the vector into a host, and producing the antibody from the host according to a conventional genetic recombination technique (see, for example, Vandamme, A. M. et al., Eur. J. Biochem. (1990) 192, 767-75).

The nucleic acid sequences of the polynucleotides encoding the variable regions (V regions) of the antibodies of the present invention can be deduced from the amino acid sequences of the V regions of the antibodies of the present invention. For example, the nucleic acid sequences shown in SEQ ID NOs: 10 and 11 may be used as the nucleic acid sequences encoding the heavy chain variable region (VH) and the light chain variable region (VL), respectively, of the antibody clone of the present invention. A polynucleotide encoding the V region of the antibodies of the present invention can be synthesized based on the sequence information by conventional methods such as the solid phase techniques (Beaucage SL & Iyer RP, Tetrahedron (1992) 48, 2223-311; Matthes et al., EMBO J (1984) 3, 801-5) and oligonucleotide synthesis techniques (Jones et al. Nature (1986) 321, 522-5).

The polynucleotide encoding the antibody V region are integrated into an expression vector containing polynucleotide encoding the antibody constant (C) region.

For the production of the antibody used in the present invention, the polynucleotide encoding the antibody (antibody gene) is integrated into an expression vector so that the antibody gene can be expressed under the control of expression control elements (e.g., enhancer, promoter). A host cell is transformed with the expression vector to express the antibody.

In the expression of the antibody gene, the polynucleotide encoding H chain and polynucleotide encoding L chain of the antibody may be integrated into separate expression vectors, and then a host cell is co-transformed with the resultant recombinant expression vectors. Alternatively, both polynucleotide encoding H chain and polynucleotide encoding L chain of the antibody may be integrated together into a single expression vector, and then a host cell is transformed with the resultant recombinant expression vector (for example, WO 94/11523).

The antibody gene can be expressed by known methods. For the expression in a mammalian cell, a conventional useful promoter, the antibody gene to be expressed and a poly(A) signal (located downstream to the 3' end of the antibody gene) may be operably linked. For example, as the useful promoter/enhancer system, a human cytomegalovirus immediate early promoter/enhancer system may be used.

Other promoter/enhancer systems, for example, those derived from viruses (e.g., retrovirus, polyoma virus, adenovirus and simian virus 40 (SV40)) and those derived from mammalian cells (e.g., human elongation factor 1 alpha (HEF1α)), may also be used for the expression of the antibody in the present invention.

When an SV40 promoter/enhancer system is used, the gene expression may be performed readily by the method of Mulligan et al. (Nature (1979) 277, 108-14). When an HEF1α promoter/enhancer system is used, the gene expression may be performed readily by the method of Mizushima et al. (Nucleic Acids Res. (1990) 18, 5322).

For the expression in E. coli, a conventional useful promoter, a signal sequence for secreting the antibody of interest and the antibody gene may be operably linked. As the promoter, lacZ promoter or araB promoter may be used. When lacZ promoter is used, the gene expression may be performed by the method of Ward et al. (Nature (1098) 341, 544-6; FASBE J. (1992) 6, 2422-7), while when araB promoter is used, the gene expression may be performed by the method of Better et al. (Science (1988) 240, 1041-3).

With respect to the signal sequence for secretion of the antibody, when the antibody of interest is intended to be secreted in a periplasmic space of the E. coli, pelB signal sequence (Lei, S. P. et al, J. Bacteriol. (1987) 169, 4379-83.) may be used. The antibody secreted into the periplasmic space is isolated and then refolded so that the antibody takes an appropriate configuration.

The replication origin derived from viruses (e.g., SV40, polyoma virus, adenovirus, bovine papilloma virus (BPV)) or the like may be used. In order to increase the gene copy number in the host cell system, the expression vector may further contain a selective marker gene, such as an aminoglycoside phosphotransferase (APH) gene, a thymidine kinase (TK) gene, an E. coli xanthine-guanine phosphoribosyltransferase (Ecogpt) gene and a dihydrofolate reductase (dhfr) gene. For the production of the antibody used in the present invention, any expression system including eukaryotic and prokaryotic cell systems may be used. The eukaryotic cell includes established cell lines of animals (e.g., mammals, insects, molds and fungi, yeast). The prokaryotic cell includes bacterial cells such as E. coli cells. It is preferable that the antibody used in the present invention be expressed in a mammalian cell, such as a CHO, COS, myeloma, BHK, Vero and HeLa cell.

Next, the transformed host cell is cultured in vitro or in vivo to produce the antibody of interest. The cultivation of the host cell may be performed by any known method. The culture medium that can be used herein may be DMEM, MEM, RPMI-1640 or IMDM medium. The culture medium may contain a serum supplement, such as fetal calf serum (FCS).

In the production of the recombinant antibody, besides the above-mentioned host cells, a transgenic animal may also be used as a host. For example, the antibody gene is inserted into a predetermined site of a gene encoding a protein inherently produced in the milk of an animal (e.g., beta-casein) to prepare a fusion gene. A DNA fragment containing the antibody gene-introduced fusion gene is injected into an embryo of a non-human animal, and the embryo is then introduced into a female animal. The female animal having the embryo therein bears a transgenic non-human animal. The antibody of interest is secreted in the milk from the transgenic non-human animal or a progeny thereof. For the purpose of increasing the amount of the antibody-containing milk, an appropriate hormone may be administered to the transgenic animal (Ebert, K. M. et al, Bio/Technology (1994) 12, 699-702).

The antibody expressed and produced as described above may be isolated from the cells or the host animal body and purified. The isolation and purification of the antibody used in the present invention may be performed on an affinity column. Other methods conventionally used for the isolation and purification of an antibody may be also be used; thus the method is not particularly limited. For example, various chromatographies, filtration, ultrafiltration, salting out and dialysis may be used singly or in combination to isolate and purify the antibody of interest (Antibodies A Laboratory Manual. Ed. Harlow, David Lane, Cold Spring Harbor Laboratory, 1988).

(ii) Antibody Fragments

Various techniques have been developed for the production of antibody fragments. Conventionally, these fragments used to be obtained through proteolytic digestion of intact antibodies (see for example, Morimoto et al., Journal of Biochemical and Biophysical Methods 24: 107-117 (1992); and Brennan et al., Science, 229: 81 (1985)). However, currently these fragments can be produced directly by recombinant host cells. For example, antibody fragments can be isolated from an antibody phage library. Alternatively, Fab'-SH fragments may be collected directly from *Escherichia coli*, and F(ab')$_2$ fragments can be formed by chemical coupling (Carter et al., Bio/Technology 10: 163-167 (1992)). In another approach, F(ab')$_2$ fragments can be directly isolated from a recombinant host cell culture. Other techniques for producing antibody fragments should be clear to those skilled in the art. In another embodiment, the most suitable antibodies are single-chain Fv fragments (scFv). See WO93/16185; U.S. Pat. Nos. 5,571,894; and 5,587,458. Furthermore, antibody fragments may be "linear antibodies" as described, for example, in U.S. Pat. No. 5,641,870. Such linear antibody fragments may be monospecific or bispecific.

(iii) Labeled Antibodies

The antibodies of the present invention are optionally conjugated with an affinity label, an enzyme label, a radioisotope label, a fluorescent label, or a chemiluminescent label. For example, the presence of a label that is present and detectable in a FZD10-expressing cancer tissue enables determination of the presence or absence of cancer or tumor in a subject diagnosed. Localization of the label in the cancer tissue also enables determination of expansion of the disease.

Labels appropriate for use include, for example, fluorescent labels such as fluorescein and rhodamine; and enzyme labels such as luciferase. Detectable labels/labels for detection to be used are selected according to the mode of imaging used. Conjugates between such labels and antibodies can be produced using protocols and techniques known in the art. In the present invention, the antibodies of the present invention may be conjugated with a desired label immediately before use, or may be provided as label-conjugated antibodies.

Conjugates between antibodies and labels can be produced using various bifunctional protein coupling agents, such as N-succinimidyl-3-(2-pyridyldithio)propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Alternatively, fusion proteins containing an antibody and a label can be produced, for example by recombination techniques or peptide synthesis. Suitable examples of such fusion proteins include fusion proteins formed between an antibody and a labeling protein such as ECFP, EYFP, or EGFP.

III. Diagnosis of FZD10-Related Diseases, Screening for Subjects in Whom Treatment with a FZD10 Inhibitor is Highly Effective (Pre-Treatment Diagnosis), or Determination of Drug Efficacy after Treatment with a FZD10 Inhibitor (Post-Treatment Diagnosis)

FZD10 is useful as a diagnostic marker for FZD10-related diseases, and as a marker for evaluating responsiveness to FZD10 inhibitors and drug efficacy of the inhibitors in subjects who suffer from the diseases. Therefore, the antibodies of the present invention can be used as reagents for detecting a marker to diagnose FZD10-related diseases such as cancer, screen for subjects in whom treatment with a FZD10 inhibitor is highly effective, or determine drug efficacy after treatment with a FZD10 inhibitor.

More specifically, the antibodies of the present invention can be used to detect a FZD10 protein in samples isolated from subjects, and diagnose FZD10-related diseases, screen for subjects in whom treatment with a FZD10 inhibitor is highly effective, or determine drug efficacy after treatment with a FZD10 inhibitor. Therefore, the present invention provides methods for diagnosing FZD10-related diseases or predispositions for developing such diseases in subjects, methods of screening for subjects in whom treatment with a FZD10 inhibitor is highly effective, and methods for determining drug efficacy after treatment with a FZD10 inhibitor, which are performed by detecting a FZD10 protein in samples isolated from the subjects using an antibody of the present invention. These methods include the following steps:

(a) contacting a sample isolated from the subject with an antibody or antigen-binding fragment thereof of the present invention;

(b) detecting the FZD10 protein in the sample by detecting binding between the antibody or antigen-binding fragment thereof and the sample; and (c) comparing the FZD10 protein level in the sample to the control.

In a typical embodiment, the sample is a cell or tissue isolated from the above-mentioned subject, and is preferably a tissue isolated from the subject. Therefore, usually, all methods of the present invention are performed in vitro on samples isolated from subjects. Methods of isolating tissues and cells from subjects by techniques such as biopsy and blood collection are known. Alternatively, biological samples removed from subjects through medical procedures for therapy (such as surgical operation) may also be used. Cells and tissues isolated from subjects can be treated appropriately before contact with antibodies. For example, generally, tissue samples obtained from subjects are frozen, sectioned, and then fixed with alcohol, formalin, and such to prepare samples for immunohistological analysis. Alternatively, tissue samples, cultured cells, and such, can be fixed with formalin and such and then embedded in paraffin to obtain sections for immunohistological analysis.

Binding of an antibody or antigen-binding fragment thereof of the present invention with a sample, or more specifically, with an antigen protein in the sample, can be detected by methods known to those skilled in the art. More specifically, after contacting the antibody of the present invention with the aforementioned sample, the antibody not bound to FZD10 in the sample is removed by washing, and then binding between the antibody of the present invention and the FZD10 protein in the sample can be detected by detecting the antibody remaining in the sample. In so doing, when the antibody is directly labeled, the presence of the antibody of the present invention bound to the FZD10 protein can be detected by detecting the label. If the label is an enzyme, fluorescent substance, luminescent substance, particle, or such which is detectable, the label can be detected immediately. In addition, when the antibody of the present invention is labeled with an affinity substance (binding substance) such as biotin (affinity labeled), the presence of the antibody can be captured using a binding partner such as labeled avidin. Alternatively, when the antibody of the present invention is not directly labeled, the antibody of the present invention can be detected with an antibody-binding reagent. For example, as an antibody-binding reagent, protein A or an anti-antibody antibody can be labeled and used for the antibody detection.

In the diagnosis of FZD10-related diseases, if the FZD10 protein level is higher than the control level (normal control level, preferably the expression level of the FZD10 protein in a sample isolated from a healthy subject who does not suffer from FZD10-related diseases) in the aforementioned step (c), this indicates that the subject suffers from a FZD10-related disease or has a risk of developing the disease.

Furthermore, in the screening for subjects in whom treatment with a FZD10 inhibitor is highly effective, if the FZD10 protein level is about the same as or higher than the control level (preferably, the expression level of the FZD10 protein in a tissue of a subject who has been diagnosed with a FZD10-related disease) in the aforementioned step (c), this indicates that treatment with a FZD10 inhibitor is highly effective in the subject.

On the other hand, in the determination of drug efficacy after treatment with a FZD10 inhibitor, if the FZD10 protein level is lower than the control level (preferably the expression level of the FZD10 protein in a sample isolated from the subject before drug administration) in the aforementioned step (c), this indicates that the drug has been effective in the subject.

Patients shown to have a FZD10-related disease according to a diagnosis method of the present invention are likely to become subjects of treatment with a FZD10 inhibitor. Therefore, following the diagnosis method of the present invention, a FZD10 inhibitor may be administered to patients shown to have a FZD10-related disease. Alternatively, after the screening, a FZD10 inhibitor can also be administered to patients in whom treatment with a FZD10 inhibitor has been shown to be likely to be highly effective. Furthermore, if the FZD10 inhibitor has been shown to have a therapeutic effect in a patient to whom the FZD10 inhibitor has been administered, administration of the FZD10 inhibitor to the same patient can be continued.

Thus, the present invention relates to methods for treating FZD10-related diseases, which comprise identifying any patient selected from the following group by a method of the present invention, and administering a FZD10 inhibitor to the patient:

a patient who has been shown to have a FZD10-related disease by a diagnosis method of the present invention;

a patient in whom treatment with an FZD10 inhibitor has been shown to be likely to be effective; and a patient who has received administration of an FZD10 inhibitor and in whom the inhibitor has been shown to have a therapeutic effect.

In the present invention, the FZD10 inhibitor to be administered to patients may be any known compound. Herein, the FZD10 inhibitor also includes antibodies showing cytotoxic activity against FZD10-expressing cells, and double stranded RNA molecules that suppress FZD10 expression. Examples of such antibodies and double stranded RNA molecules are antibodies against FZD10 disclosed in WO2005/004912 or WO2007/148417, and FZD10-specific siRNA disclosed in WO2006/013733.

In the context of the present invention, a control level measured from a biological sample known to be free of FZD10-related diseases (for example, non-cancerous) is called a "normal control level". When the FZD10 protein level in a sample isolated from a subject is higher than the normal control level, the subject may be diagnosed with a FZD10-related disease which should be treated.

On the other hand, a control level determined from a biological sample known to have a FZD10-related disease (for example, cancerous) is called a "disease control level (for example, cancerous control level)". When the FZD10 protein level in a sample isolated from a subject before treatment with a FZD10 inhibitor is equal to or higher than the disease control level, it may be diagnosed that treatment with a FZD10 inhibitor is highly effective in the subject.

Furthermore, when the FZD10 protein level in a sample isolated from a subject after treatment with a FZD10 inhibitor is lower than the disease control level of the same subject before drug administration, it may be diagnosed that the treatment has been effective, in other words, the treatment with a FZD10 inhibitor is highly effective.

In a certain embodiment, normal cells (or tissues) obtained from a non-diseased region (for example, non-cancerous region) of an organ with a FZD10-related disease to be treated (for example, cancer) may be used as a normal control. In another embodiment, the control level can be determined by a statistical method based on results obtained by analyzing the FZD10 protein level measured in advance in samples derived from subjects whose disease state (for example, cancerous or non-cancerous) is known. Furthermore, the control level may be derived from a database of expression patterns derived from previously tested samples (cells or tissues). When the samples to be evaluated are tissue samples, a sample derived from the same tissue is preferably used as a control sample.

Furthermore, according to one aspect of the present invention, the FZD10 protein level in a biological sample can be compared to a plurality of control levels measured from a plurality of reference samples. It is preferred to use control levels measured from reference samples derived from a tissue type similar to the tissue type of the biological sample derived from the subject. It is further preferred to use a reference value of the FZD10 protein level in a population whose disease state is known. The reference value can be obtained by any method known in the art. For example, the reference value used can be a range of mean+/−2 S.D. or mean+/−3 S.D.

The FZD10 protein level in a sample can be considered to be high when the level is, for example, 10%, 25%, or 50% higher than the control level, or more than 1.1 times, more than 1.5 times, more than 2.0 times, more than 5.0 times, or more than 10.0 times higher than the control level, or even higher. The FZD10 protein level in a sample can be considered to be low when the level is, for example, 10%, 25%, or 50% lower than the control level, or more than 1.1 times, more than 1.5 times, more than 2.0 times, more than 5.0 times, or more than 10.0 times lower than the control level, or even lower.

In a typical embodiment, the FZD10-related disease is a FZD10-expressing cancer. FZD10-expressing cancers are, for example, synovial sarcoma, lung cancer, esophageal cancer, colorectal cancer (large intestine cancer), stomach cancer, chronic myeloid leukemia (CML), and acute myeloid leukemia (AML), but are not limited thereto.

In a further embodiment, the present invention provides methods for detecting a diagnostic marker for a FZD10-related disease or a predisposition for developing the disease, wherein the methods comprise detecting a FZD10 protein in a sample as the diagnostic marker by using an antibody or antigen binding fragment thereof of the present invention. It has been shown that FZD10 expression is enhanced in certain types of cancer cells as compared to normal tissues. Therefore, if the FZD10 expression level can be detected specifically, this will be useful as a diagnostic marker for FZD10-related diseases. In the context of the present invention, a diagnostic marker for a FZD10-related disease or a predisposition for developing the disease refers to a FZD10 protein in a sample isolated from a subject, which is detected by means of binding with an antibody or antigen-binding fragment thereof of the present invention, and it is characterized in that when its expression level is higher than the control level, the subject is shown to suffer from the disease or has a risk of developing the disease. Here, the aforementioned control level is a normal control level, and preferably the FZD10 protein expression level in a sample isolated from a healthy subject who does not suffer from a FZD10-related disease. Generally, the control level is preferably an expression level in the same tissue as the tissue from which cancer cells subjected to diagnostic marker detection are derived.

The present invention also provides the antibody or antigen-binding fragment thereof of the present invention for use in diagnosing a FZD10-related disease or a predisposition for developing the disease. Alternatively, the present invention provides use of the antibody or antigen-binding fragment thereof of the present invention in manufacture of a reagent for diagnosing a FZD10-related disease or a predisposition for developing the disease.

In addition, the present invention provides methods for detecting a marker for responsiveness to FZD10 inhibitor treatment, wherein the methods comprise the step of detecting a FZD10 protein in a sample as the responsiveness marker using an antibody or antigen-binding fragment thereof of the present invention. It has been shown that FZD10 expression is enhanced specifically in certain cancer cells and the growth of such cancer cells is suppressed by FZD10 inhibitors (WO2005/004912, WO2006/013733, and WO2007/148417). That is, FZD10 expression can be used as an indicator for predicting responsiveness to FZD10 inhibitors. This is because if FZD10 is expressed at a high level, FZD10 inhibitors can be expected to have a cell growth inhibitory effect. Therefore, if FZD10 expression level can be specifically detected, this will be useful as a marker for responsiveness to FZD10 inhibitor treatment. In the context of the present invention, a marker for responsiveness to FZD10 inhibitor treatment refers to a FZD10 protein in a sample isolated from a subject, which is detected by means of binding with an antibody or antigen-binding fragment thereof of the present invention, and is characterized in that when its expression level is equal to or higher than the control level, the effect of treatment with a FZD10 inhibitor is shown to be high in the subject. Here, the aforementioned control level is preferably a disease control level, i.e. the FZD10 protein expression level in a sample isolated from a diseased site of a subject known to suffer from a FZD10-related disease, and is particularly preferably the FZD10 protein expression level in a sample isolated before treatment from a subject in whom treatment with a FZD10 inhibitor is highly effective.

The present invention also provides the antibody or antigen-binding fragment thereof of the present invention for use in screening for a subject in whom treatment with a FZD10 inhibitor is highly effective. Alternatively, the present invention provides use of the antibody or antigen- binding fragment thereof of the present invention in manufacture of a reagent for screening for a subject in whom treatment with a FZD10 inhibitor is highly effective.

The present invention also provides methods for detecting a marker for the drug efficacy of a FZD10 inhibitor, wherein the methods comprise the step of detecting a FZD10 protein in a sample as the drug efficacy marker using an antibody or antigen-binding fragment thereof of the present invention. It has been shown that FZD10 expression is enhanced specifically in certain cancer cells, and the growth of such cancer cells is suppressed by FZD10 inhibitors (WO2005/004912, WO2006/013733, and WO2007/148417). Therefore, cancer tissues carrying such cancer cells may be diminished or killed by FZD10 inhibitors. That is, the FZD10 expression level can be used as an indicator to evaluate the drug efficacy of FZD10 inhibitors in subjects carrying such cancer cells. This is because if the FZD10 expression level in a sample isolated from a tissue carrying FZD10-positive cancer cells is decreased compared to the level of a sample isolated before FZD10 inhibitor treatment, it can be considered that the FZD10 inhibitor has decreased the FZD10-positive cancer cells. Therefore, if the FZD10 expression level can be detected specifically, it will be useful as a marker for the drug efficacy of FZD10 inhibitors. In the context of the present invention, a marker for the drug efficacy of FZD10 inhibitors refers to a FZD10 protein in a sample isolated from a subject who has received FZD10 inhibitor administration, which is detected by means of binding with an antibody or antigen-binding fragment thereof of the present invention, and is characterized in that when its expression level is lower than the control level, the FZD10 inhibitor is shown to have been effective in the subject. Here, the aforementioned control level is preferably the expression level of the FZD10 protein in a sample isolated from a diseased site of the subject before drug administration.

The present invention also provides the antibody or antigen-binding fragment thereof of the present invention for use in determining drug efficacy after treatment with a FZD10 inhibitor. Alternatively, the present invention provides use of the antibody or antigen-binding fragment thereof of the present invention in manufacture of a reagent for determining drug efficacy after treatment with a FZD10 inhibitor.

IV. Reagents or Kits for Diagnosis of FZD10-Related Diseases, Screening for Subjects in Whom Treatment with a FZD10 Inhibitor is Highly Effective, or Determination of Drug Efficacy after Treatment with a FZD10 Inhibitor The present invention provides reagents or kits for diagnosis of FZD10-related diseases, screening for subjects in whom treatment with a FZD10 inhibitor is highly effective, or determination of drug efficacy after treatment with a FZD10 inhibitor. Specifically, these kits contain an antibody or antigen-binding fragment thereof of the present invention as a FZD10 protein-detection reagent. In one embodiment, the antibody for the diagnostic reagent or kit of the present invention can be labeled with a fluorescent substance, a luminescent substance, or a radioisotope. Methods for labeling an antibody and methods for detecting a labeled antibody are well known in the art, and any label and method may be used for the present invention.

The present kits can include a combination of the antibody or antigen-binding fragment thereof of the present invention and another marker detection reagent. The kits can further include positive and negative control reagents for FZD10, and a secondary antibody for detection of the antibody of the present invention. For example, culture sections of cell lines or tissue samples known to highly express FZD10 may serve as useful positive control reagents. Furthermore, for example, tissue samples obtained from healthy subjects or noncancerous tissues may serve as useful negative control reagents. The secondary antibody for detecting the antibody of the present invention is preferably labeled with a fluorescent substance, a luminescent substance, a radioisotope, or an enzyme. The kits of the present invention may further include other materials desired from the user's standpoint or the commercial viewpoint, including a buffer, a dilution solution, a filter, a needle, a syringe, and an attached document with instructions for use (for example, a written document, tape, and CD-ROM). These reagents and such can be retained in a labeled container. Appropriate containers include bottles, vials, and test tubes. The containers may be made of various materials such as glass or plastic.

The present invention is explained herein in detail with reference to its specific embodiments. However, it should be understood that the above explanation is in fact an illustrative and explanatory explanation, and is intended to explain the present invention and preferred embodiments thereof. Through routine experimentation, one skilled in the art will readily recognize that various changes and modifications can be made therein without departing from the spirit and scope of the present invention. Thus, the present invention is not confined to the above explanation, but is intended to be defined by the appended claims and equivalents thereto.

Hereinbelow, the present invention is described in more detail with reference to the Examples. Nevertheless, while the following materials, method and Examples may serve to assist one of ordinary skill in making and using certain embodiments of the present invention, there are only intended to illustrate aspects of the present invention and thus in no way to limit the scope of the present invention. One of ordinary skill in the art can use methods and materials similar or equivalent to those described herein in the practice or testing of the present invention.

All prior art documents cited herein are incorporated by reference in the present specification.

EXAMPLES

Next, the present invention will be specifically described with reference to the Examples, but it is not to be construed as being limited thereto.

[Materials and Methods]

Cell Culture

A FZD10 expression vector was introduced into the human colorectal cancer cell line DLD1 purchased from ATCC to produce a cell line forced to express FZD10 (FZD10/DLD1). A cell line into which Empty Vector was introduced (Mock/DLD1) was produced as a negative control. The cell lines were maintained in RPMI-1640 supplemented with 10% fetal bovine serum (FBS), 1% penicillin/streptomycin, and 0.8 mg/mL GENETICIN at 37° C. in a humidified atmosphere of 5% $CO_2$. Human synovial sarcoma cell line SYO-1, provided by the Rare Cancer Center of the National Cancer Center, was maintained in DMEM supplemented with 10% fetal bovine serum (FBS) and 1% penicillin/streptomycin at 37° C. in a humidified atmosphere of 5% $CO_2$. Human esophageal cancer cell line T.T, purchased from JCRB, was maintained in DMEM/F12 (1:1) supplemented with 10% fetal bovine serum (FBS) and 1% penicillin/streptomycin at 37° C. in a humidified atmosphere of 5% $CO_2$. Human lung cancer cell line H727, purchased from ATCC, was maintained in RPMI-1640 supplemented with 10% fetal bovine serum (FBS) and 1% penicillin/ streptomycin at 37° C. in a humidified atmosphere of 5% $CO_2$. Human colorectal cancer cell line COLO201, purchased from ATCC, was maintained in RPMI-1640 supplemented with 10% fetal bovine serum (FBS), 1% penicillin/ streptomycin, 10 mM HEPES, 1 mM sodium pyruvate, and 4.5 g/L glucose at 37° C. in a humidified atmosphere of 5% $CO_2$. Human colorectal cancer cell line LoVo, purchased from ATCC, was maintained in F12 supplemented with 20% fetal bovine serum (FBS) and 1% penicillin/streptomycin at 37° C. in a humidified atmosphere of $CO_2$.

Clinical Specimens

Tissue samples from surgically removed lung cancer (formalin-fixed paraffin sections and frozen tissues) and their corresponding clinical information were obtained from Kanagawa Cancer Center upon written informed consent.

Immunohistochemical Staining (IHC)

Formalin-fixed paraffin sections of FZD10/DLD1, Mock/ DLD1, SYO1, T.T, H727, LoVo, COLO201, and clinical specimens were deparaffinized by immersion in xylene for three minutes three times, and then immersed in 100% ethanol for one minute twice, followed by 90%, 70%, and 50% ethanol for one minute each for rehydration. For antigen retrieval treatment, sections immersed in Antigen Retrieval Solution pH9 (Nichirei Biosciences Inc.) were incubated at 125° C. for 30 seconds for FZD10/DLD1 and Mock/DLD1, and at 95° C. for 40 minutes for SYO1, T.T, H727, LoVo, COLO201, and clinical specimens. After incubation, they were allowed to stand at room temperature for 20 minutes, and then washed with running water for five minutes. The sections were immersed in 3.0% hydrogen peroxide for ten minutes to block endogenous peroxidases, and washed with Wash Buffer (TBS-T(Takara Bio)) for five minutes three times. Furthermore, to block nonspecific reactions, an appropriate amount of Protein Block Solution (Dako) was added dropwise onto the sections, and they were allowed to stand for ten minutes. In a moist chamber, a suitable amount of each primary antibody (FZD10Ab (10A8H4G4), FZD10(L164)pAb, and FZD10 PolyclonalAb) was added dropwise, and after allowing the sections to stand for 60 minutes, they were subjected to three five-minute washes with Wash Buffer. In a moist chamber, an appropriate amount of Histofine Simple Stain MAX-PO (Nichirei Biosciences Inc.), as the secondary antibody, was added dropwise, and allowed to stand for 30 minutes. The sections were washed with Wash Buffer for five minutes three times. Coloring reaction was performed using DAB Substrate Solution (Nichirei Biosciences Inc.). The slide sections were immersed in hematoxylin (Dako) for 20 seconds, and washed with running water. Dehydration was performed by immersion in 50%, 70%, and 90% ethanol for one minute each, and in 100% ethanol for one minute twice. Finally, the sections were cleared by immersion in xylene for three minutes twice, and mounted with Mount-Quick (DAIDO SANGYO).

Real-Time (RT) PCR

Total RNA was extracted from cancer cell lines (SYO-1 and COLO201) using RNeasy Mini kit (QIAGEN). For clinical frozen tissue (squamous lung cancer), frozen tissue sections were immersed in TRIzol Reagent (Invitrogen) and ground, and subjected to chloroform extraction. To the obtained extract, an approximately equal amount of 70% ethanol was added, and total RNA was extracted using RNeasy Mini kit (QIAGEN). Using the transcriptase of SuperScript III Reverse Transcriptase (Invitrogen), cDNA was synthesized from total RNA. Using the cDNA as a template, PCR was performed with KAPA SYBR FAST ABI Prism qPCR kit (KAPA Biosystems). The target gene for expression analysis was FZD10, and the housekeeping gene was glyceraldehyde-3-phosphate dehydrogenase (GAPDH). Real-time PCR was performed using, for FZD10, the primer set of FZD10-11F: 5'-GTGTGCAGCCGTAGGTTAAAG-3' (SEQ ID NO:12) and FZD10 R5: 5'-GACTGGGCAGG-GATCTCATA-3' (SEQ ID NO: 13), and for GAPDH, the primer set of GAPDH RT-PCR Fw: 5'-ACAACAGCCT-CAAGATCATCAG-3' (SEQ ID NO:14) and GAPDH RT-PCR Re: 5'-GGTCCACCACTGACACGTTG-3' (SEQ ID NO:15). The amount of the PCR amplification product was monitored overtime, and the Ct value was calculated by setting a threshold in the region where the PCR amplification product was being amplified exponentially. The concentration of an unknown sample was calculated by applying the Ct value to the calibration curve. The template amount was standardized among the samples by dividing the quantified value for the FZD10 gene by the quantified value for the GAPDH gene, and FZD10 gene expression levels were compared.

Flow Cytometry (FCM)

SYO1, T.T, H727, and LoVo were maintained in the respective recommended culture media until early confluence. To avoid degeneration of the cell surface antigens, the cells were then separated using a Cell Dissociation Solution (SIGMA, MO), and suspended in 0.5% BSA/PBS. The suspended cells were passed through a cell strainer to remove aggregates, and the number of cells were counted. The cells were dispensed into a 96-well assay plate ($2 \times 10^5$ cells/50 µL). 50 µL of diluted test antibody or culture supernatant was added, and allowed to stand at 4° C. for one hour. The plate was centrifuged at 1500 rpm for five minutes at 4° C., the supernatant was removed, and then the plate was washed twice with 150 µL of 0.5% BSA/PBS. The cells were mixed with 20 mg/mL of Alexa Fluor 488 goat anti-mouse IgG (H+L) (Invitrogen, CA), and allowed to stand in the dark at 4° C. for one hour. The plate was centrifuged at 1500 rpm for five minutes at 4° C., the supernatant was removed, then the plate was washed twice with 150 µL of 0.5% BSA/PBS, and the cells were suspended in 120 µL of 0.5% BSA/PBS. The binding mode and specificity of the test antibody were evaluated using FACS Calibur (Becton Dickinson, NJ) according to the manufacturer's instructions.

[Example 1] Production of Anti-FZD10 Monoclonal Antibodies (1) Acquisition of Anti-FZD10 Antibody-Producing Hybridomas Using Soluble FZD10 Protein as Immunogen FZD10 is a membrane protein. To produce antibodies that react towards a fixed membrane protein, its extracellular region may become an immunogen. Since the extracellular regions of FZD10, except for the N terminal region, are so short that they might be difficult to use as antigens, the N-terminal extracellular region (amino acids 1 to 161) was selected as an immunogen. A soluble FZD10 protein without the signal peptide (the region of amino acids 21 to 161) (SEQ ID NO: 9) was used as an immunogen to produce monoclonal antibodies. 50 µg of the antigen peptide was added to Freund's adjuvant, emulsified, and injected subcutaneously to Balb/c mice (Japan SLC, Inc.) for primary immunization. The second and later immunizations were performed by subcutaneously injecting an amount equivalent to 25 µg of the antigen peptide prepared in the same manner. Three days after the final immunization, splenocytes were aseptically prepared from mice. According to the conventional method, they were fused with SP2/0 mouse myeloma cells by the polyethylene glycol method.

(2) Selection of Anti-FZD10 Antibody-Producing Hybridomas

For selection of anti-FZD10 antibodies, first, the ELISA method was performed using the soluble FZD10 protein to screen for antibodies binding to FZD10. The antibodies selected by the ELISA method was further screened by immunological staining. Selection by immunological staining was performed by immunohistochemical staining using the FZD10 forced-expression cell line FZD10/DLD1 expressing a full length FZD10 protein (SEQ ID NO: 22). Specifically, a formalin-fixed paraffin section of the cell line FZD10/DLD1 forced to express the full length FZD10 protein was produced. Then immunological staining was carried out and hybridomas for which strong reaction was observed were selected.

Figure 2:
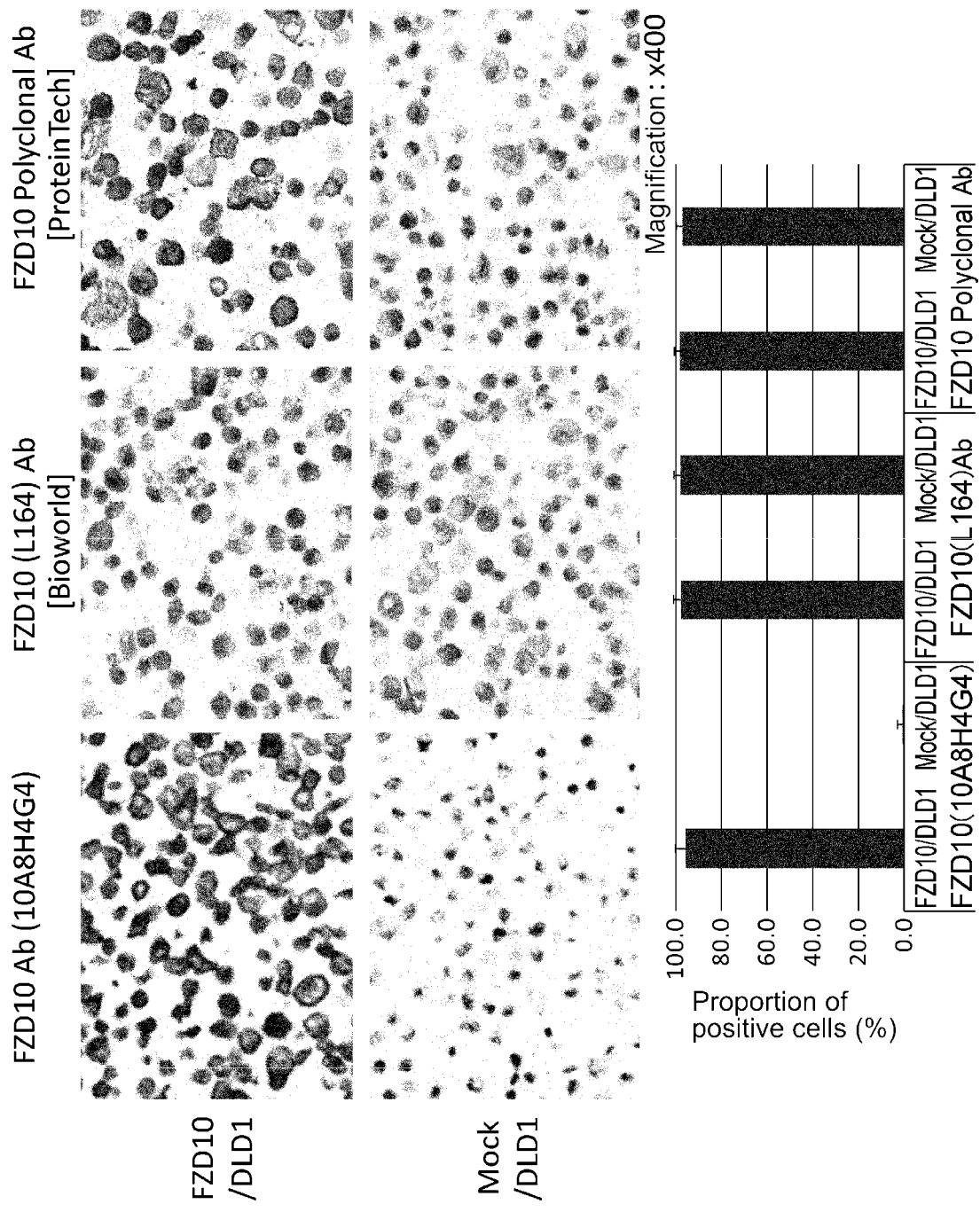
FIG. 2 is a set of photomicrographs showing the specificity of an anti-FZD10 antibody (10A8H4G4) in immunohistochemical staining using a cell line forced to express FZD10. As a result of immunohistochemical staining with the anti-FZD10 antibody (10A8H4G4), specific staining was observed on a paraffin section prepared from a cell line forced to express FZD10 (FZD10/DLD1), but no staining was observed in a cell line into which Empty Vector was introduced (Mock/DLD1) as a negative control. On the other hand, as a result of immunohistochemical staining using commercially available antibodies (FZD10(L164)Ab and FZD10PolyclonalAb), staining was observed in both FZD10/DLD1 and Mock/DLD1. This revealed the specificity of the anti-FZD10 antibody (10A8H4G4) compared to the commercially available antibodies. Furthermore, the graph below the photographs shows the proportion (%) of FZD10-positive cells to the number of the forced-expression cells, which was calculated from the result of immunohistochemical staining.

Of the tested hybridomas, the hybridoma clone 10A8H4G4 was found to produce a FZD10-specific antibody at a high level, and its immunohistochemical staining results are shown in FIG. 2. As shown in the photographs and graphs of FIG. 2, the paraffin section prepared from the FZD10 forced-expression cell line FZD10/DLD1 showed staining with 10A8H4G4, indicating that the proportion of FZD10-positive cells was high. On the other hand, the paraffin section prepared from the cell line into which Empty Vector was introduced as a negative control (Mock/DLD1) showed little staining, indicating that the proportion of FZD10-positive cells was low. These results demonstrate that the hybridoma clone 10A8H4G4 is useful as a hybridoma producing an antibody that specifically detects FZD10 in immunohistochemical staining.

On the other hand, when commercially available antibodies (FZD10(L164)Ab and FZD10PolyclonalAb) were used for staining, staining was observed in both FZD10/DLD1 and Mock/DLD1 (the signal was detected in a high proportion of cells). Therefore, the detection results with these commercial antibodies were suspected to include false-positive signals.

From the above-mentioned results, the anti-FZD10 antibody of the present invention (10A8H4G4) was found to have an advantageous property of being able to detect FZD10 with higher specificity than commercially available anti-FZD10 antibodies in immunohistochemical staining.

This hybridoma clone 10A8H4G4 was selected to produce the antibody for further experiments. Hybridoma clone 10A8H4G4 was cultured in a large scale, and the culture fluid was collected two to three weeks later. The antibody was purified from the culture fluid using a Protein A column (GE Healthcare, NJ). Herein, the antibody of the present invention is also referred to as clone 10A8H4G4.

[Example 2] Evaluation of Specificity of Anti-FZD10 Monoclonal Antibody

Next, the specificity of 10A8H4G4 was evaluated using various cell lines with different expression levels of FZD10. Specifically, the results of immunohistochemical staining and flow cytometry using 10A8H4G4 were compared to examine whether the staining was in accordance with the expression level of FZD10 protein. The Cancer Cell Line Encyclopedia (CCLE), an mRNA expression analysis database with cell lines of each cancer type, shows that the expression is remarkably upregulated in lung cancer, esophageal cancer, and colorectal cancer (large intestine cancer) (FIG. 1). Accordingly, cell lines derived from these cancer types were used in the following analysis.

Figure 3:
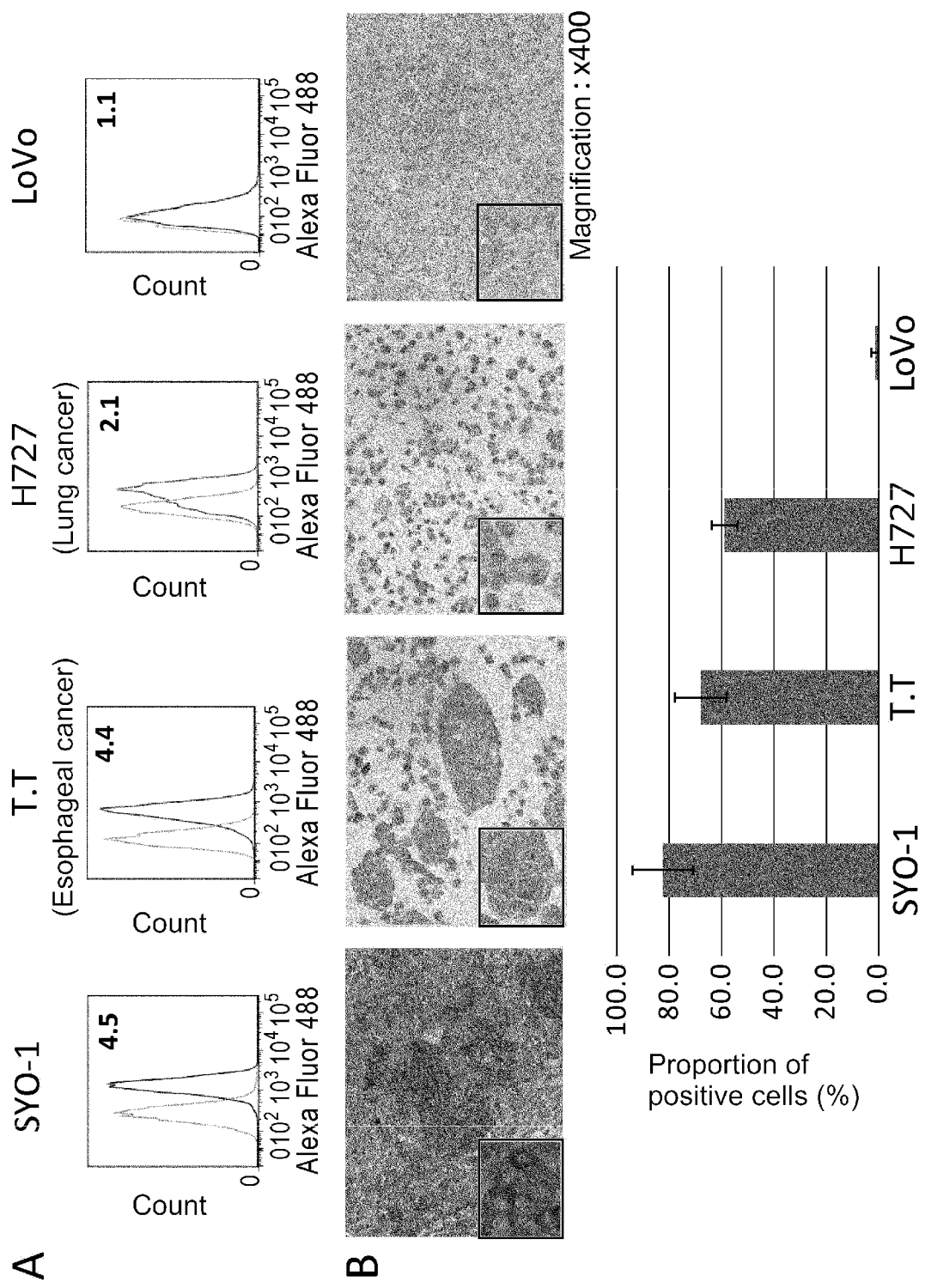
FIG. 3 shows the correlation between expression analyzed by flow cytometry and by immunohistochemical staining using various cell lines with different FZD10 expression levels. A: Histograms showing the results of flow cytometry using 10A8H4G4, which detected FZD10 expression on the cell membrane of each cell line. SYO-1, T.T, and H727 were cell lines expressing FZD10, and LoVo was a cell line not expressing FZD10. B: Photomicrographs showing the results of immunohistochemical staining using paraffin sections prepared from each cell line. The graph below the photographs shows the proportion (%) of FZD10-positive cells in each cell line, which was calculated from the result of immunohistochemical staining. Staining was observed in FZD10-expressing cell lines such as SYO-1, T.T, and H727, but not in LoVo (non-expression cell line). Analyses using cell lines revealed the specificity of the anti-FZD10 antibody (10A8H4G4) in immunohistochemical staining.

First, flow cytometry using 10A8H4G4 was performed to confirm the expression of endogenous FZD10 protein on the cell membrane of various human cancer tissue-derived cell lines. As shown in FIG. 3, positive signals were detected by flow cytometry using 10A8H4G4 in human synovial sarcoma-derived SYO-1, which is known to express the FZD10 protein endogenously, and also in human esophageal cancer-derived cell line T.T and human lung cancer-derived cell line H727. On the other hand, no positive signal was detected by flow cytometry using 10A8H4G4 in human colorectal cancer-derived cell line LoVo, which is known as a non-FZD10-expressing cell line.

Next, immunohistochemical staining using 10A8H4G4 was performed on paraffin sections prepared from these cell lines. As shown in FIG. 3B, as a result of staining with 10A8H4G4, staining was observed in the paraffin sections prepared from SYO-1, T.T, and H727, the cell lines which had been found to express FZD10. In these paraffin sections, positive signals were detected in a high proportion of cells in correlation with the flow cytometry results. On the other hand, there was little staining in the paraffin section prepared from non-FZD10-expressing cell line LoVo, with almost no positive signal detected.

The above-mentioned results demonstrate that the anti-FZD10 antibody of the present invention (10A8H4G4) is a useful tool that can detect a FZD10 protein within samples in both flow cytometry and immunohistochemical staining with high specificity.

[Example 3] Detection of FZD10 Protein in Tumor Graft Model and Clinical Specimens The specificity of the anti-FZD10 antibody of the present invention (10A8H4G4) in immunohistochemical staining was evaluated using paraffin sections prepared from mouse xenograft tumors of cancer cell lines and clinical lung cancer specimens. The expression of FZD10 protein and RNA in paraffin sections prepared from mouse xenograft tumors of SYO-1 and COLO201 and in cancerous and non-cancerous regions of clinical lung cancer specimens 1 to 6 was detected by immunohistochemical staining and real-time PCR, respectively, and the results are shown in FIG. 4.

Figure 4:
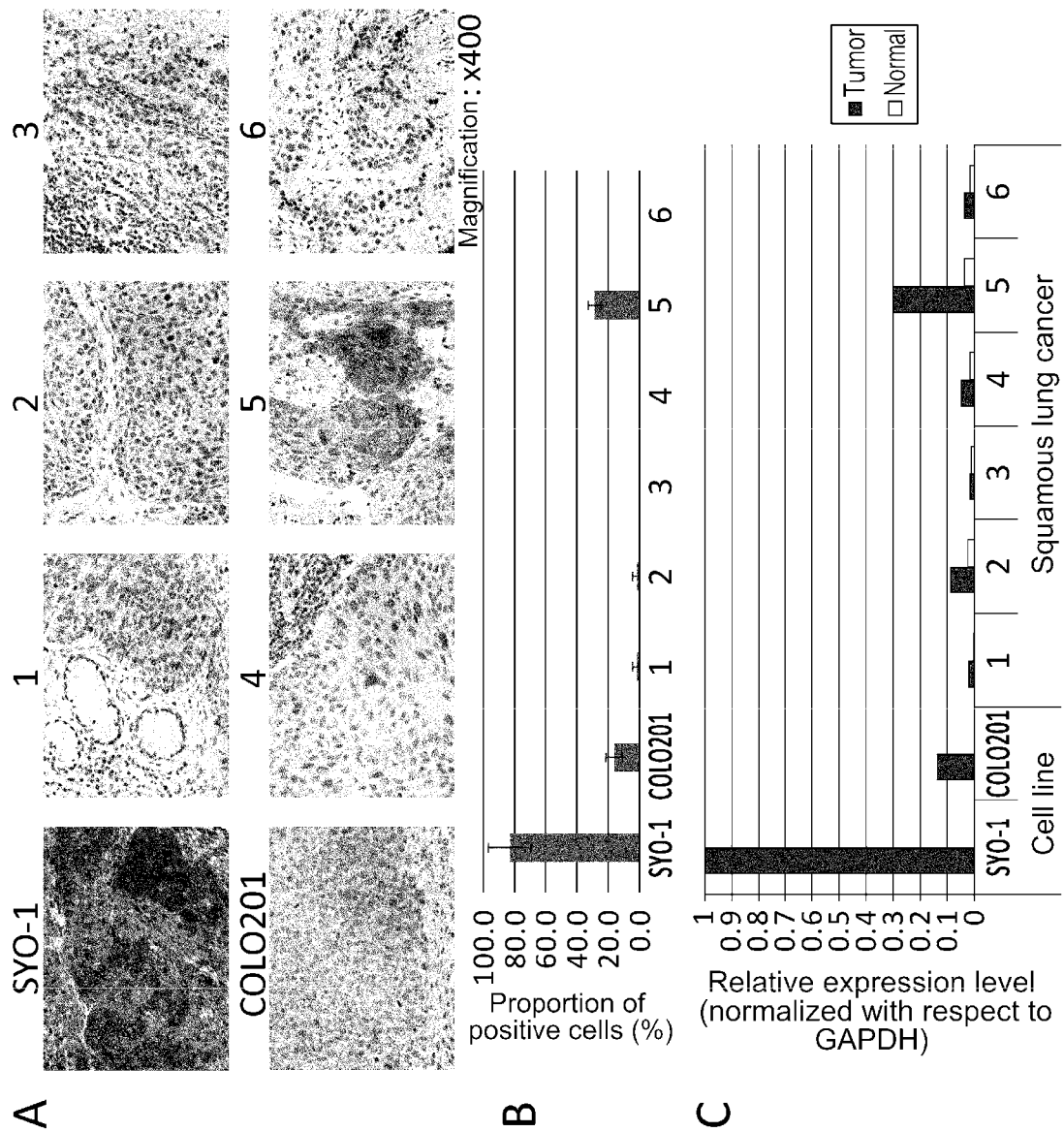
FIG. 4 shows the correlation between expression analyzed by immunohistochemical staining and by real-time PCR using paraffin sections prepared from mouse xenograft tumors of SYO-1 and COLO201 cell lines and clinical lung cancer specimens 1 to 6. A: In immunohistochemical staining using the anti-FZD10 antibody of the present invention (10A8H4G4), SYO-1 and specimen 5 were found to be FZD10 positive. On the other hand, there was little staining in low-expression specimens. B: The proportion of FZD10-positive cells to the tumor cells calculated from the immunohistochemical staining results of A is presented as a graph. C: Expression analyses of the same cases by real-time PCR gave results that correlated with immunohistochemical staining. Analyses using clinical specimens revealed the high specificity of the anti-FZD10 antibody of the present invention (10A8H4G4) in immunohistochemical staining.

As shown in FIG. 4, in the paraffin section prepared from a mouse xenograft tumor of the SYO-1 cell line, which was found to highly express FZD10 RNA, cells stained with 10A8H4G4, i.e. FZD10-positive cells, were detected. However, in the paraffin section prepared from a mouse xenograft tumor of COLO201, the cell line in which the amount of FZD10 RNA expression was small, the number of cells stained with 10A8H4G4, i.e. FZD10-positive cells, was also small. This result demonstrates that the anti-FZD10 antibody of the present invention (10A8H4G4) is a useful tool for obtaining detection results in immunohistochemical staining that correlate with FZD10 protein expression levels within samples.

Furthermore, in lung cancer clinical specimen 5, in which tumor region-specific FZD10 RNA expression was observed, cells stained with 10A8H4G4, i.e. FZD10-positive cells, were detected. However, the other clinical lung cancer specimens, in which tumor region-specific FZD10 RNA expression was not observed, were hardly stained, with almost no FZD10-positive cell detected. This result demonstrates that 10A8H4G4 can specifically detect the FZD10 protein in clinical specimens as well.

[Example 4] Analysis of Amino Acid Sequences of Variable Regions of Anti-FZD10 Monoclonal Antibody The amino acid sequences of the variable regions of the anti-FZD10 antibody of the present invention (10A8H4G4) were analyzed.

Using RNeasy mini kit (QIAGEN), total RNA was extracted from hybridoma 10A8H4G4. cDNA was synthesized from the total RNA using Super Script II Reverse Transcriptase (Invitrogen). Primers for cDNA synthesis are the following.

```
mIGCUniRv as a heavy chain 3'-primer:
                                    (SEQ ID NO: 16)
    5'-CTGGGAAGGTGTGCACAC-3' mIGKRv2 as a light chain 3' primer:
                                    (SEQ ID NO: 17)
    5'-GTTGTTCAAGAAGCACACGAC-3'
```

A polymer of dC was added to the end of the cDNA using 5' RACE System for Rapid Amplification of cDNA Ends (Invitrogen), and polynucleotides encoding the variable regions of the monoclonal antibody were amplified using Platinum Taq DNA Polymerase High Fidelity (Invitrogen). Primers for amplification are the following. Nucleotide "I" in the primer sequence represents inosine.

```
5' RACE Abridged Anchor Primer as heavy chain 5'
and light chain 5' primers:
                                    (SEQ ID NO: 18)
5'-GGCCACGCGTCGACTAGTACGGGIIGGGIIGGGIIG-3';

mIGCUniRv2 as a heavy chain 3'-primer:
                                    (SEQ ID NO: 19)
5'-TGGACAGGGATCCAGAGTTCC-3';
and mIGKNesRv2 as a light chain 3' primer:
                                    (SEQ ID NO: 20)
5'-CAGATGTTAACTGCTCACTGGATGG-3'.
```

PCR products were cloned into pGEM-T Easy Vector (Promega). The sequences of the insert fragment regions were determined, and the nucleotide sequences of the variable regions of 10A8H4G4 (excluding the signal sequence) were determined.

The amino acid sequences and the nucleotide sequences of the heavy chain variable region and the light chain variable region of the mouse monoclonal antibody were determined as follows:

```
10A8H4G4, amino acid sequence of heavy chain
variable region (excluding the signal sequence):
(encoded by the nucleotide sequence
of SEQ ID NO: 10)
                                    (SEQ ID NO: 7)
QVTLKESGPGILQPSQTLSLTCSFSGFSLSTSGLGVSWIRQPSGKGLE

WLAHIYWDDDKRYNPSLKSRLTISKDTSSNQVFLKITSVDTADTATYY

CARRAYYGNYYALDYWGQGTSVTVSS;

10A8H4G4, nucleotide sequence of heavy chain
variable region:
                                    (SEQ ID NO: 10)
5'-CAGGTTACTCTGAAAGAGTCTGGCCCTGGGATATTGCAGCCCTCC

CAGACCCTCAGTCTGACTTGTTCTTTCTCTGGGTTTTCACTGAGCACT
```

```
TCTGGTCTGGGTGTGAGCTGGATTCGTCAGCCTTCAGGAAAGGGTCTG

GAGTGGCTGGCACACATTTACTGGGATGATGACAAGCGCTATAACCCA

TCCCTGAAGAGCCGGCTCACAATCTCCAAGGATACCTCCAGCAACCAG

GTATTCCTCAAGATCACCAGTGTGGACACTGCAGATACTGCCACATAC

TACTGTGCTCGAAGAGCCTACTATGGTAATTACTATGCTTTGGACTAC

TGGGGTCAAGGAACCTCAGTCACCGTCTCCTCA-3';

10A8H4G4, amino acid sequence of light chain
variable region (excluding the signal sequence):
(encoded by the nucleotide sequence
of SEQ ID NO: 11)
                                    (SEQ ID NO: 8)
DIVMTQSPSSLTVTAGEKVTMSCKSSQSLLNSGNQKNYLTWYQQKPGQ

PPKLLIYWASTRKSGVPDRFTGSGSGTDFTLTISSVQAEDLAVYYCQN

DYSYPVTFGAGTKLELKRAD;

10A8H4G4, nucleotide sequence of light chain
variable region:
                                    (SEQ ID NO: 11)
5'-GACATTGTGATGACACAGTCTCCATCCTCCCTGACTGTGACA

GCAGGAGAGAAGGTCACTATGAGCTGCAAGTCCAGTCAGAGTCTGTTA

AACAGTGGAAATCAAAAGAACTACTTGACCTGGTACCAGCAGAAACCA

GGGCAGCCTCCTAAACTGTTGATCTACTGGGCATCCACTAGGAAATCT

GGGGTCCCTGATCGCTTCACAGGCAGTGGATCTGGAACAGATTTCACT

CTCACCATCAGCAGTGTGCAGGCTGAAGACCTGGCAGTTTATTACTGT

CAGAATGATTATAGTTATCCGGTCACGTTCGGTGCTGGGACCAAGCTG

GAGCTGAAACGGGCTGAT-3'.
```

The CDR sequences of the antibody of the present invention (10A8H4G4) determined according to the definition by Kabat are as follows:

```
heavy chain CDR1 (CDR-H1):
                                    (SEQ ID NO: 1)
TSGLGVS;

heavy chain CDR2 (CDR-H2):
                                    (SEQ ID NO: 2)
HIYWDDDKRYNPSLKS;

heavy chain CDR3 (CDR-H3):
                                    (SEQ ID NO: 3)
RAYYGNYYALDY;

light chain CDR1 (CDR-L1):
                                    (SEQ ID NO: 4)
KSSQSLLNSGNQKNYLT;

light chain CDR2 (CDR-L2):
                                    (SEQ ID NO: 5)
WASTRKS;
and light chain CDR3 (CDR-L3):
                                    (SEQ ID NO: 6)
QNDYSYPVT.
```

INDUSTRIAL APPLICABILITY

The present invention succeeded in producing an anti-FZD10 antibody capable of detecting a FZD10 protein in samples isolated from targets such as clinical specimens with high specificity. Use of the anti-FZD10 antibody of the present invention allows highly-sensitive, low-background detection of FZD10 protein in samples. Therefore, the antibody of the present invention is useful in diagnosing FZD10-related diseases such as FZD10-expressing cancers. Furthermore, since the antibody of the present invention can detect FZD10 in accordance with the expression level of FZD10 in samples, it is also useful in screening for subjects in whom treatment with a FZD10 inhibitor is highly effective (pre-treatment diagnosis), and determining drug efficacy after treatment with a FZD10 inhibitor in subjects (post-treatment diagnosis).

The invention claimed is:

1. An antibody or antigen-binding fragment thereof capable of binding to a FZD10 protein or a partial peptide thereof, which comprises both of:
   a heavy chain variable region comprising
   CDR1 comprising the amino acid sequence of SEQ ID NO: 1,
   CDR2 comprising the amino acid sequence of SEQ ID NO: 2, and
   CDR3 comprising the amino acid sequence of SEQ ID NO: 3; and
   a light chain variable region comprising
   CDR1 comprising the amino acid sequence of SEQ ID NO: 4,
   CDR2 comprising the amino acid sequence of SEQ ID NO: 5, and
   CDR3 comprising the amino acid sequence of SEQ ID NO: 6.

2. The antibody or antigen-binding fragment thereof of claim 1, which comprises both of a heavy chain variable region comprising the amino acid sequence of SEQ ID NO: 7 and a light chain variable region comprising the amino acid sequence of SEQ ID NO: 8.

3. The antibody or antigen-binding fragment thereof of claim 1, which specifically recognizes a polypeptide consisting of the amino acid sequence of SEQ ID NO: 9.

4. The antibody or antigen-binding fragment thereof of claim 1, which is conjugated with an affinity label, an enzyme label, a radioisotope label, or a fluorescent label.

5. A polynucleotide encoding the antibody or antigen-binding fragment thereof of claim 1.

6. A reagent for diagnosing a FZD10-related disease, determining drug efficacy after treatment with a FZD10 inhibitor, or screening for a subject in whom treatment with a FZD10 inhibitor is highly effective, wherein the reagent comprises the antibody or antigen-binding fragment thereof of claim 1.

7. A method for diagnosing a FZD10-related disease or a predisposition for developing the disease in a subject, wherein the method comprises the steps of:
   (a) contacting a sample isolated from the subject with the antibody or antigen-binding fragment thereof of claim 1;
   (b) detecting a FZD10 protein in the sample by detecting binding between the antibody or antigen-binding fragment thereof and the sample; and
   (c) comparing the level of the FZD10 protein in the sample to a control, wherein a higher FZD10 protein level than the control indicates that the subject suffers from the disease or has a risk of developing the disease.

8. The reagent of claim 6, wherein the FZD10-related disease is a cancer expressing FZD10.

9. The reagent of claim 8, wherein the cancer is selected from the group consisting of synovial sarcoma, lung cancer, esophageal cancer, colorectal cancer (large intestine cancer), stomach cancer, chronic myeloid leukemia (CML), and acute myeloid leukemia (AML).

10. A method for detecting a FZD10 protein in a sample, which comprises the steps of:
    (a) contacting a sample isolated from a subject with the antibody or antigen-binding fragment thereof of claim 1; and
    (b) detecting a FZD10 protein in the sample by detecting binding between the antibody or antigen-binding fragment thereof and the sample.

11. A method for determining drug efficacy after treatment with a FZD10 inhibitor in a subject, wherein the method comprises the steps of:
    (a) contacting a sample isolated from the subject with the antibody or antigen-binding fragment thereof of claim 1;
    (b) detecting a FZD10 protein in the sample by detecting binding between the antibody or antigen-binding fragment thereof and the sample; and (c) comparing the level of the FZD10 protein in the sample to the expression level before administration of the drug, wherein a FZD10 protein level lower than that before administration of the drug indicates that the drug has been effective in the subject.

12. A method of screening for a subject in whom treatment with a FZD10 inhibitor is highly effective, wherein the method comprises the steps of:
(a) contacting a sample isolated from the subject with the antibody or antigen-binding fragment thereof of claim 1;
(b) detecting a FZD10 protein in the sample by detecting binding between the antibody or antigen-binding fragment thereof and the sample; and
(c) comparing the FZD10 protein level in the sample to a control, wherein a FZD10 protein level equal to or higher than the control indicates that treatment with a FZD10 inhibitor is highly effective in the subject.

13. The method of claim 7, wherein the sample is a cell or tissue isolated from the subject.

14. A method for producing an antibody or antigen-binding fragment thereof that can bind to a FZD10 protein or a partial peptide thereof, wherein the method comprises the steps of:
(a) culturing a cell comprising a vector into which the polynucleotide of claim 5 has been introduced; and
(b) collecting the antibody from a culture or culture medium of the cell.

15. The method of claim 7, wherein the FZD10-related disease is a cancer expressing FZD10.

16. The method of claim 15, wherein the cancer is selected from the group consisting of synovial sarcoma, lung cancer, esophageal cancer, colorectal cancer (large intestine cancer), stomach cancer, chronic myeloid leukemia (CML), and acute myeloid leukemia (AML).

* * * * *

SEQUENCE LISTING

```
<160> NUMBER OF SEQ ID NOS: 22

<210> SEQ ID NO 1
<211> LENGTH: 7
<212> TYPE: PRT
<213> ORGANISM: Artificial Sequence
<220> FEATURE:
<223> OTHER INFORMATION: VH CDR1

<400> SEQUENCE: 1

Thr Ser Gly Leu Gly Val Ser
1               5

<210> SEQ ID NO 2
<211> LENGTH: 16
<212> TYPE: PRT
<213> ORGANISM: Artificial Sequence
<220> FEATURE:
<223> OTHER INFORMATION: VH CDR2

<400> SEQUENCE: 2

His Ile Tyr Trp Asp Asp Asp Lys Arg Tyr Asn Pro Ser Leu Lys Ser
1               5                   10                  15

<210> SEQ ID NO 3
```

```
<211> LENGTH: 12
<212> TYPE: PRT
<213> ORGANISM: Artificial Sequence
<220> FEATURE:
<223> OTHER INFORMATION: VH CDR3

<400> SEQUENCE: 3

Arg Ala Tyr Tyr Gly Asn Tyr Tyr Ala Leu Asp Tyr
1               5                   10

<210> SEQ ID NO 4
<211> LENGTH: 17
<212> TYPE: PRT
<213> ORGANISM: Artificial Sequence
<220> FEATURE:
<223> OTHER INFORMATION: VL CDR1

<400> SEQUENCE: 4

Lys Ser Ser Gln Ser Leu Leu Asn Ser Gly Asn Gln Lys Asn Tyr Leu
1               5                   10                  15

Thr

<210> SEQ ID NO 5
<211> LENGTH: 7
<212> TYPE: PRT
<213> ORGANISM: Artificial Sequence
<220> FEATURE:
<223> OTHER INFORMATION: VL CDR2

<400> SEQUENCE: 5

Trp Ala Ser Thr Arg Lys Ser
1               5

<210> SEQ ID NO 6
<211> LENGTH: 9
<212> TYPE: PRT
<213> ORGANISM: Artificial Sequence
<220> FEATURE:
<223> OTHER INFORMATION: VL CDR

<400> SEQUENCE: 6

Gln Asn Asp Tyr Ser Tyr Pro Val Thr
1               5

<210> SEQ ID NO 7
<211> LENGTH: 122
<212> TYPE: PRT
<213> ORGANISM: Artificial Sequence
<220> FEATURE:
<223> OTHER INFORMATION: H-chain variable region

<400> SEQUENCE: 7

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
                20                  25                  30

Gly Leu Gly Val Ser Trp Ile Arg Gln Pro Ser Gly Lys Gly Leu Glu
            35                  40                  45

Trp Leu Ala His Ile Tyr Trp Asp Asp Lys Arg Tyr Asn Pro Ser
    50                  55                  60

Leu Lys Ser Arg Leu Thr Ile Ser Lys Asp Thr Ser Ser Asn Gln Val
65                  70                  75                  80

Phe Leu Lys Ile Thr Ser Val Asp Thr Ala Asp Thr Ala Thr Tyr Tyr
                85                  90                  95
```

Cys Ala Arg Arg Ala Tyr Tyr Gly Asn Tyr Tyr Ala Leu Asp Tyr Trp
            100                 105                 110

Gly Gln Gly Thr Ser Val Thr Val Ser Ser
        115                 120

<210> SEQ ID NO 8
<211> LENGTH: 116
<212> TYPE: PRT
<213> ORGANISM: Artificial Sequence
<220> FEATURE:
<223> OTHER INFORMATION: L-chain variable region

<400> SEQUENCE: 8

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Lys Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Val Thr Phe Gly Ala Gly Thr Lys Leu Glu Leu
            100                 105                 110

Lys Arg Ala Asp
        115

<210> SEQ ID NO 9
<211> LENGTH: 141
<212> TYPE: PRT
<213> ORGANISM: Artificial Sequence
<220> FEATURE:
<223> OTHER INFORMATION: FZD10 fragment for immunogen

<400> SEQUENCE: 9

Ile Ser Ser Met Asp Met Glu Arg Pro Gly Asp Gly Lys Cys Gln Pro
1               5                   10                  15

Ile Glu Ile Pro Met Cys Lys Asp Ile Gly Tyr Asn Met Thr Arg Met
            20                  25                  30

Pro Asn Leu Met Gly His Glu Asn Gln Arg Glu Ala Ala Ile Gln Leu
        35                  40                  45

His Glu Phe Ala Pro Leu Val Glu Tyr Gly Cys His Gly His Leu Arg
    50                  55                  60

Phe Phe Leu Cys Ser Leu Tyr Ala Pro Met Cys Thr Glu Gln Val Ser
65                  70                  75                  80

Thr Pro Ile Pro Ala Cys Arg Val Met Cys Glu Gln Ala Arg Leu Lys
                85                  90                  95

Cys Ser Pro Ile Met Glu Gln Phe Asn Phe Lys Trp Pro Asp Ser Leu
            100                 105                 110

Asp Cys Arg Lys Leu Pro Asn Lys Asn Asp Pro Asn Tyr Leu Cys Met
        115                 120                 125

Glu Ala Pro Asn Asn Gly Ser Asp Glu Pro Thr Arg Gly
        130                 135                 140

```
<210> SEQ ID NO 10
<211> LENGTH: 366
<212> TYPE: DNA
<213> ORGANISM: Artificial Sequence
<220> FEATURE:
<223> OTHER INFORMATION: H-chain variable region nucleic acid sequence

<400> SEQUENCE: 10
caggttactc tgaaagagtc tggccctggg atattgcagc cctcccagac cctcagtctg     60
acttgttctt tctctgggtt ttcactgagc acttctggtc tgggtgtgag ctggattcgt    120
cagccttcag gaaagggtct ggagtggctg gcacacattt actgggatga tgacaagcgc    180
tataacccat ccctgaagag ccggctcaca atctccaagg atacctccag caaccaggta    240
ttcctcaaga tcaccagtgt ggacactgca gatactgcca catactactg tgctcgaaga    300
gcctactatg gtaattacta tgctttggac tactggggtc aaggaacctc agtcaccgtc    360
tcctca                                                               366

<210> SEQ ID NO 11
<211> LENGTH: 348
<212> TYPE: DNA
<213> ORGANISM: Artificial Sequence
<220> FEATURE:
<223> OTHER INFORMATION: L-chain variable region nucleic acid sequence

<400> SEQUENCE: 11
gacattgtga tgacacagtc tccatcctcc ctgactgtga cagcaggaga gaaggtcact     60
atgagctgca gtccagtca gagtctgtta acagtggaa atcaaaagaa ctacttgacc      120
tggtaccagc agaaaccagg gcagcctcct aaactgttga tctactgggc atccactagg    180
aaatctgggg tccctgatcg cttcacaggc agtggatctg gaacagattt cactctcacc    240
atcagcagtg tgcaggctga agacctggca gtttattact gtcagaatga ttatagttat    300
ccggtcacgt tcggtgctgg gaccaagctg gagctgaaac gggctgat                 348

<210> SEQ ID NO 12
<211> LENGTH: 21
<212> TYPE: DNA
<213> ORGANISM: Artificial Sequence
<220> FEATURE:
<223> OTHER INFORMATION: An artificially synthesized forward primer
      sequence for FZD10

<400> SEQUENCE: 12
gtgtgcagcc gtaggttaaa g                                               21

<210> SEQ ID NO 13
<211> LENGTH: 20
<212> TYPE: DNA
<213> ORGANISM: Artificial Sequence
<220> FEATURE:
<223> OTHER INFORMATION: An artificially synthesized reverse primer
      sequence for FZD10

<400> SEQUENCE: 13
gactgggcag ggatctcata                                                 20

<210> SEQ ID NO 14
<211> LENGTH: 22
<212> TYPE: DNA
<213> ORGANISM: Artificial Sequence
<220> FEATURE:
<223> OTHER INFORMATION: An artificially synthesized forward primer
      sequence for GAPDH
```

<400> SEQUENCE: 14
acaacagcct caagatcatc ag                                                    22

<210> SEQ ID NO 15
<211> LENGTH: 20
<212> TYPE: DNA
<213> ORGANISM: Artificial Sequence
<220> FEATURE:
<223> OTHER INFORMATION: An artificially synthesized reverse primer
      sequence for GAPDH

<400> SEQUENCE: 15
ggtccaccac tgacacgttg                                                       20

<210> SEQ ID NO 16
<211> LENGTH: 18
<212> TYPE: DNA
<213> ORGANISM: Artificial Sequence
<220> FEATURE:
<223> OTHER INFORMATION: An artificially synthesized 3' primer sequence
      for VH

<400> SEQUENCE: 16
ctgggaaggt gtgcacac                                                         18

<210> SEQ ID NO 17
<211> LENGTH: 21
<212> TYPE: DNA
<213> ORGANISM: Artificial Sequence
<220> FEATURE:
<223> OTHER INFORMATION: An artificially synthesized 3' primer sequence
      for VL

<400> SEQUENCE: 17
gttgttcaag aagcacacga c                                                     21

<210> SEQ ID NO 18
<211> LENGTH: 36
<212> TYPE: DNA
<213> ORGANISM: Artificial Sequence
<220> FEATURE:
<223> OTHER INFORMATION: An artificially synthesized 5' primer sequence
      for VH and VL
<220> FEATURE:
<221> NAME/KEY: misc_feature
<222> LOCATION: (24)..(25)
<223> OTHER INFORMATION: n is inosine
<220> FEATURE:
<221> NAME/KEY: misc_feature
<222> LOCATION: (29)..(30)
<223> OTHER INFORMATION: n is inosine
<220> FEATURE:
<221> NAME/KEY: misc_feature
<222> LOCATION: (34)..(35)
<223> OTHER INFORMATION: n is inosine

<400> SEQUENCE: 18
ggccacgcgt cgactagtac gggnngggnn gggnng                                     36

<210> SEQ ID NO 19
<211> LENGTH: 21
<212> TYPE: DNA
<213> ORGANISM: Artificial Sequence
<220> FEATURE:
<223> OTHER INFORMATION: An artificially synthesized 3' primer sequence
      for VH

<400> SEQUENCE: 19

```
tggacaggga tccagagttc c                                              21

<210> SEQ ID NO 20
<211> LENGTH: 25
<212> TYPE: DNA
<213> ORGANISM: Artificial Sequence
<220> FEATURE:
<223> OTHER INFORMATION: An artificially synthesized 3' primer sequence
      for VL

<400> SEQUENCE: 20
cagatgttaa ctgctcactg gatgg                                          25

<210> SEQ ID NO 21
<211> LENGTH: 3288
<212> TYPE: DNA
<213> ORGANISM: Homo sapiens
<220> FEATURE:
<221> NAME/KEY: CDS
<222> LOCATION: (485)..(2230)
<300> PUBLICATION INFORMATION:
<308> DATABASE ACCESSION NUMBER: Genbank acc no. NM_007197.3
<309> DATABASE ENTRY DATE: 2015-12-31
<313> RELEVANT RESIDUES IN SEQ ID NO: (1)..(3288)

<400> SEQUENCE: 21
cgagtcttct catcccggga cgcaaacctc gaaacagctg ccggctggtc ccggccgagg    60
ccggcgcagg gagggaggag ccgccgggc tgtgggggcg ccgcgagctg ggccggcctc    120
ggtgtgcccg cgccgccagc ccgctccaga cgcgccacct gggcgctcca agaagaggcc    180
gaagtttgcc gcggccgtga gttggagctc cgccgggcc gctgcgccgg gagctccggg    240 ggcttcctc gcttcccggt attgtttgca aactttgctg ctctccgccg cggccccaa    300 ctcggcggac gccgggcgcg gagagccgag ccggggggcg tgtgcgcagc gctcgggcca    360
ggccgggcgg gcatgggcgg gggcccgagc aggggtggag agccggggcc agcagcagcc    420
cgtgcccggg agcggcggcg ctgaggggcg cggagctccc cgcgaggaca cgtccaacgc    480 cagc atg cag cgc ccg ggc ccc cgc ctg tgg ctg gtc ctg cag gtg atg    529
     Met Gln Arg Pro Gly Pro Arg Leu Trp Leu Val Leu Gln Val Met
     1                5                  10                  15 ggc tcg tgc gcc gcc atc agc tcc atg gac atg gag cgc ccg ggc gac    577
Gly Ser Cys Ala Ala Ile Ser Ser Met Asp Met Glu Arg Pro Gly Asp
                 20                  25                  30 ggc aaa tgc cag ccc atc gag atc ccg atg tgc aag gac atc ggc tac    625
Gly Lys Cys Gln Pro Ile Glu Ile Pro Met Cys Lys Asp Ile Gly Tyr
             35                  40                  45 aac atg act cgt atg ccc aac ctg atg ggc cac gag aac cag cgc gag    673
Asn Met Thr Arg Met Pro Asn Leu Met Gly His Glu Asn Gln Arg Glu
         50                  55                  60 gca gcc atc cag ttg cac gag ttc gcg ccg ctg gtg gag tac ggc tgc    721
Ala Ala Ile Gln Leu His Glu Phe Ala Pro Leu Val Glu Tyr Gly Cys
     65                  70                  75 cac ggc cac ctc cgc ttc ttc ctg tgc tcg ctg tac gcg ccg atg tgc    769
His Gly His Leu Arg Phe Phe Leu Cys Ser Leu Tyr Ala Pro Met Cys
 80                  85                  90                  95 acc gag cag gtc tct acc ccc atc ccc gcc tgc cgg gtc atg tgc gag    817
Thr Glu Gln Val Ser Thr Pro Ile Pro Ala Cys Arg Val Met Cys Glu
                100                 105                 110 cag gcc cgg ctc aag tgc tcc ccg att atg gag cag ttc aac ttc aag    865
Gln Ala Arg Leu Lys Cys Ser Pro Ile Met Glu Gln Phe Asn Phe Lys
            115                 120                 125
```

```
tgg ccc gac tcc ctg gac tgc cgg aaa ctc ccc aac aag aac gac ccc     913
Trp Pro Asp Ser Leu Asp Cys Arg Lys Leu Pro Asn Lys Asn Asp Pro
        130                 135                 140 aac tac ctg tgc atg gag gcg ccc aac aac ggc tcg gac gag ccc acc    961
Asn Tyr Leu Cys Met Glu Ala Pro Asn Asn Gly Ser Asp Glu Pro Thr
145                 150                 155 cgg ggc tcg ggc ctg ttc ccg ccg ctg ttc cgg ccg cag cgg ccc cac   1009
Arg Gly Ser Gly Leu Phe Pro Pro Leu Phe Arg Pro Gln Arg Pro His
160                 165                 170                 175 agc gcg cag gag cac ccg ctg aag gac ggg ggc ccc ggg cgc ggc ggc   1057
Ser Ala Gln Glu His Pro Leu Lys Asp Gly Gly Pro Gly Arg Gly Gly
            180                 185                 190 tgc gac aac ccg ggc aag ttc cac cac gtg gag aag agc gcg tcg tgc   1105
Cys Asp Asn Pro Gly Lys Phe His His Val Glu Lys Ser Ala Ser Cys
                195                 200                 205 gcg ccg ctc tgc acg ccc ggc gtg gac gtg tac tgg agc cgc gag gac   1153
Ala Pro Leu Cys Thr Pro Gly Val Asp Val Tyr Trp Ser Arg Glu Asp
        210                 215                 220 aag cgc ttc gca gtg gtc tgg ctg gcc atc tgg gcg gtg ctg tgc ttc   1201
Lys Arg Phe Ala Val Val Trp Leu Ala Ile Trp Ala Val Leu Cys Phe
225                 230                 235 ttc tcc agc gcc ttc acc gtg ctc acc ttc ctc atc gac ccg gcc cgc   1249
Phe Ser Ser Ala Phe Thr Val Leu Thr Phe Leu Ile Asp Pro Ala Arg
240                 245                 250                 255 ttc cgc tac ccc gag cgc ccc atc atc ttc ctc tcc atg tgc tac tgc   1297
Phe Arg Tyr Pro Glu Arg Pro Ile Ile Phe Leu Ser Met Cys Tyr Cys
            260                 265                 270 gtc tac tcc gtg ggc tac ctc atc cgc ctc ttc gcc ggc gcc gag agc   1345
Val Tyr Ser Val Gly Tyr Leu Ile Arg Leu Phe Ala Gly Ala Glu Ser
                275                 280                 285 atc gcc tgc gac cgg gac agc ggc cag ctc tat gtc atc cag gag gga   1393
Ile Ala Cys Asp Arg Asp Ser Gly Gln Leu Tyr Val Ile Gln Glu Gly
        290                 295                 300 ctg gag agc acc ggc tgc acg ctg gtc ttc ctg gtc ctc tac tac ttc   1441
Leu Glu Ser Thr Gly Cys Thr Leu Val Phe Leu Val Leu Tyr Tyr Phe
305                 310                 315 ggc atg gcc agc tcg ctg tgg tgg gtg gtc ctc acg ctc acc tgg ttc   1489
Gly Met Ala Ser Ser Leu Trp Trp Val Val Leu Thr Leu Thr Trp Phe
320                 325                 330                 335 ctg gcc gcc ggc aag aag tgg ggc cac gag gcc atc gaa gcc aac agc   1537
Leu Ala Ala Gly Lys Lys Trp Gly His Glu Ala Ile Glu Ala Asn Ser
            340                 345                 350 agc tac ttc cac ctg gca gcc tgg gcc atc ccg gcg gtg aag acc atc   1585
Ser Tyr Phe His Leu Ala Ala Trp Ala Ile Pro Ala Val Lys Thr Ile
                355                 360                 365 ctg atc ctg gtc atg cgc agg gtg gcg ggg gac gag ctc acc ggg gtc   1633
Leu Ile Leu Val Met Arg Arg Val Ala Gly Asp Glu Leu Thr Gly Val
        370                 375                 380 tgc tac gtg ggc agc atg gac gtc aac gcg ctc acc ggc ttc gtg ctc   1681
Cys Tyr Val Gly Ser Met Asp Val Asn Ala Leu Thr Gly Phe Val Leu
385                 390                 395 att ccc ctg gcc tgc tac ctg gtc atc ggc acg tcc ttc atc ctc tcg   1729
Ile Pro Leu Ala Cys Tyr Leu Val Ile Gly Thr Ser Phe Ile Leu Ser
400                 405                 410                 415 ggc ttc gtg gcc ctg ttc cac atc cgg agg gtg atg aag acg ggc ggc   1777
Gly Phe Val Ala Leu Phe His Ile Arg Arg Val Met Lys Thr Gly Gly
            420                 425                 430 gag aac acg gac aag ctg gag aag ctc atg gtg cgt atc ggg ctc ttc   1825
Glu Asn Thr Asp Lys Leu Glu Lys Leu Met Val Arg Ile Gly Leu Phe
                435                 440                 445
```

```
tct gtg ctg tac acc gtg ccg gcc acc tgt gtg atc gcc tgc tac ttt      1873
Ser Val Leu Tyr Thr Val Pro Ala Thr Cys Val Ile Ala Cys Tyr Phe
        450                 455                 460 tac gaa cgc ctc aac atg gat tac tgg aag atc ctg gcg gcg cag cac      1921
Tyr Glu Arg Leu Asn Met Asp Tyr Trp Lys Ile Leu Ala Ala Gln His
465                 470                 475 aag tgc aaa atg aac aac cag act aaa acg ctg gac tgc ctg atg gcc      1969
Lys Cys Lys Met Asn Asn Gln Thr Lys Thr Leu Asp Cys Leu Met Ala
480                 485                 490                 495 gcc tcc atc ccc gcc gtg gag atc ttc atg gtg aag atc ttt atg ctg      2017
Ala Ser Ile Pro Ala Val Glu Ile Phe Met Val Lys Ile Phe Met Leu
                500                 505                 510 ctg gtg gtg ggg atc acc agc ggg atg tgg att tgg acc tcc aag act      2065
Leu Val Val Gly Ile Thr Ser Gly Met Trp Ile Trp Thr Ser Lys Thr
            515                 520                 525 ctg cag tcc tgg cag cag gtg tgc agc cgt agg tta aag aag aag agc      2113
Leu Gln Ser Trp Gln Gln Val Cys Ser Arg Arg Leu Lys Lys Lys Ser
        530                 535                 540 cgg aga aaa ccg gcc agc gtg atc acc agc ggt ggg att tac aaa aaa      2161
Arg Arg Lys Pro Ala Ser Val Ile Thr Ser Gly Gly Ile Tyr Lys Lys
545                 550                 555 gcc cag cat ccc cag aaa act cac cac ggg aaa tat gag atc cct gcc      2209
Ala Gln His Pro Gln Lys Thr His His Gly Lys Tyr Glu Ile Pro Ala
560                 565                 570                 575 cag tcg ccc acc tgc gtg tga acagggctgg agggaagggc acaggggcgc         2260
Gln Ser Pro Thr Cys Val
                580 ccggagctaa gatgtggtgc ttttcttggt tgtgttttc tttcttcttc ttctttttttt    2320 tttttataa aagcaaaaga gaaatacata aaaaagtgtt taccctgaaa ttcaggatgc     2380 tgtgatacac tgaaaggaaa aatgtactta aagggttttg ttttgttttg gttttccagc    2440 gaagggaagc tcctccagtg aagtagcctc ttgtgtaact aatttgtggt aaagtagttg    2500 attcagccct cagaagaaaa cttttgttta gagccctccc taaatataca tctgtgtatt    2560 tgagttggct ttgctaccca tttacaaata agaggacaga taactgcttt gcaaattcaa    2620 gagcctcccc tgggttaaca aatgagccat ccccagggcc cacccccagg aaggccacag    2680 tgctgggcgg catccctgca gaggaaagac aggacccggg gcccgcctca caccccagtg    2740 gatttggagt tgcttaaaat agactccggc cttaccaat agtctctctg caagacagaa     2800 acctccatca aacctcacat tgtgaactc aaacgatgtg caatacatttt ttttctcttt    2860 ccttgaaaat aaaagagaa acaagtattt tgctatatat aaagacaaca aaagaaatct     2920 cctaacaaaa gaactaagag gcccagcct cagaaaccct tcagtgctac attttgtggc     2980 ttttaatgg aaaccaagcc aatgttatag acgtttggac tgatttgtgg aaaggagggg     3040 ggagaggga gaaggatcat tcaaaagtta cccaaagggc ttattgactc tttctattgt     3100 taaacaaatg atttccacaa acagatcagg aagcactagg ttggcagaga cactttgtct    3160 agtgtattct cttcacagtg ccaggaaaga gtggtttctg cgtgtgtata tttgtaatat    3220 atgatatttt tcatgctcca ctatttattt aaaaataaaa tatgttcttt agtttgctgc    3280 taaaaaaa                                                             3288

<210> SEQ ID NO 22
<211> LENGTH: 581
<212> TYPE: PRT
<213> ORGANISM: Homo sapiens
```

```
<400> SEQUENCE: 22

Met Gln Arg Pro Gly Pro Arg Leu Trp Leu Val Leu Gln Val Met Gly
1               5                   10                  15

Ser Cys Ala Ala Ile Ser Ser Met Asp Met Glu Arg Pro Gly Asp Gly
            20                  25                  30

Lys Cys Gln Pro Ile Glu Ile Pro Met Cys Lys Asp Ile Gly Tyr Asn
        35                  40                  45

Met Thr Arg Met Pro Asn Leu Met Gly His Glu Asn Gln Arg Glu Ala
    50                  55                  60

Ala Ile Gln Leu His Glu Phe Ala Pro Leu Val Glu Tyr Gly Cys His
65                  70                  75                  80

Gly His Leu Arg Phe Phe Leu Cys Ser Leu Tyr Ala Pro Met Cys Thr
                85                  90                  95

Glu Gln Val Ser Thr Pro Ile Pro Ala Cys Arg Val Met Cys Glu Gln
            100                 105                 110

Ala Arg Leu Lys Cys Ser Pro Ile Met Glu Gln Phe Asn Phe Lys Trp
        115                 120                 125

Pro Asp Ser Leu Asp Cys Arg Lys Leu Pro Asn Lys Asn Asp Pro Asn
    130                 135                 140

Tyr Leu Cys Met Glu Ala Pro Asn Asn Gly Ser Asp Glu Pro Thr Arg
145                 150                 155                 160

Gly Ser Gly Leu Phe Pro Pro Leu Phe Arg Pro Gln Arg Pro His Ser
                165                 170                 175

Ala Gln Glu His Pro Leu Lys Asp Gly Gly Pro Gly Arg Gly Gly Cys
            180                 185                 190

Asp Asn Pro Gly Lys Phe His His Val Glu Lys Ser Ala Ser Cys Ala
        195                 200                 205

Pro Leu Cys Thr Pro Gly Val Asp Val Tyr Trp Ser Arg Glu Asp Lys
    210                 215                 220

Arg Phe Ala Val Val Trp Leu Ala Ile Trp Ala Val Leu Cys Phe Phe
225                 230                 235                 240

Ser Ser Ala Phe Thr Val Leu Thr Phe Leu Ile Asp Pro Ala Arg Phe
                245                 250                 255

Arg Tyr Pro Glu Arg Pro Ile Ile Phe Leu Ser Met Cys Tyr Cys Val
            260                 265                 270

Tyr Ser Val Gly Tyr Leu Ile Arg Leu Phe Ala Gly Ala Glu Ser Ile
        275                 280                 285

Ala Cys Asp Arg Asp Ser Gly Gln Leu Tyr Val Ile Gln Glu Gly Leu
    290                 295                 300

Glu Ser Thr Gly Cys Thr Leu Val Phe Leu Val Leu Tyr Tyr Phe Gly
305                 310                 315                 320

Met Ala Ser Ser Leu Trp Trp Val Val Leu Thr Leu Thr Trp Phe Leu
                325                 330                 335

Ala Ala Gly Lys Lys Trp Gly His Glu Ala Ile Glu Ala Asn Ser Ser
            340                 345                 350

Tyr Phe His Leu Ala Ala Trp Ala Ile Pro Ala Val Lys Thr Ile Leu
        355                 360                 365

Ile Leu Val Met Arg Arg Val Ala Gly Asp Glu Leu Thr Gly Val Cys
    370                 375                 380

Tyr Val Gly Ser Met Asp Val Asn Ala Leu Thr Gly Phe Val Leu Ile
385                 390                 395                 400

Pro Leu Ala Cys Tyr Leu Val Ile Gly Thr Ser Phe Ile Leu Ser Gly
                405                 410                 415
```

```
Phe Val Ala Leu Phe His Ile Arg Arg Val Met Lys Thr Gly Gly Glu
            420             425             430

Asn Thr Asp Lys Leu Glu Lys Leu Met Val Arg Ile Gly Leu Phe Ser
            435             440             445

Val Leu Tyr Thr Val Pro Ala Thr Cys Val Ile Ala Cys Tyr Phe Tyr
    450             455             460

Glu Arg Leu Asn Met Asp Tyr Trp Lys Ile Leu Ala Ala Gln His Lys
465             470             475             480

Cys Lys Met Asn Asn Gln Thr Lys Thr Leu Asp Cys Leu Met Ala Ala
                485             490             495

Ser Ile Pro Ala Val Glu Ile Phe Met Val Lys Ile Phe Met Leu Leu
            500             505             510

Val Val Gly Ile Thr Ser Gly Met Trp Ile Trp Thr Ser Lys Thr Leu
            515             520             525

Gln Ser Trp Gln Gln Val Cys Ser Arg Arg Leu Lys Lys Lys Ser Arg
    530             535             540

Arg Lys Pro Ala Ser Val Ile Thr Ser Gly Gly Ile Tyr Lys Lys Ala
545             550             555             560

Gln His Pro Gln Lys Thr His His Gly Lys Tyr Glu Ile Pro Ala Gln
            565             570             575

Ser Pro Thr Cys Val
            580
```